US006855865B2

(12) United States Patent
Famodu et al.

(10) Patent No.: US 6,855,865 B2
(45) Date of Patent: Feb. 15, 2005

(54) NUCLEIC ACIDS ENCODING PLANT DEFENSINS AND METHODS OF USE THEREOF

(75) Inventors: Omolayo O. Famodu, Newark, DE (US); Rafael Herrmann, Wilmington, DE (US); Albert L. Lu, Newark, DE (US); Billy Fred McCutchen, Clive, IA (US); Guo-Hua Miao, Johnston, IA (US); James K. Presnail, Avondale, PA (US); Zude Weng, Warsaw, IN (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/178,449

(22) Filed: Jun. 21, 2002

(65) Prior Publication Data

US 2003/0140368 A1 Jul. 24, 2003

Related U.S. Application Data

(63) Continuation-in-part of application No. 10/030,516, filed as application No. PCT/US00/11952 on May 3, 2000, now abandoned.

(60) Provisional application No. 60/133,039, filed on May 7, 1999.

(51) Int. Cl.[7] ........................ C12N 15/09; C12N 15/29; C11N 15/82; A01H 5/00; A01H 5/10

(52) U.S. Cl. ........................ 800/279; 800/278; 800/298; 800/295; 800/320; 800/317; 435/320.1; 435/468; 435/419; 536/23.6

(58) Field of Search ................................ 800/278, 279, 800/298, 295, 320, 317; 435/320.1, 419, 468; 536/23.6

(56) References Cited

U.S. PATENT DOCUMENTS 4,945,050 A 7/1990 Sanford et al. ............. 435/459
5,412,839 A 5/1995 McCollom
5,421,839 A * 6/1995 Ulbrich et al. ................ 514/12
5,538,525 A 7/1996 Broekaert et al. ............. 514/2
5,689,043 A 11/1997 Broekaert et al. .......... 800/301
5,750,504 A 5/1998 Broekaert et al.
5,773,694 A 6/1998 Broekaert et al.
5,773,696 A 6/1998 Liang et al. ................ 800/279
5,824,869 A 10/1998 Broekaert et al. .......... 800/301
5,847,047 A 12/1998 Haynie ...................... 525/54.1
5,861,480 A 1/1999 Attenborough et al.
5,919,918 A 7/1999 Broekaert et al.
6,150,588 A 11/2000 Attenborough et al.
6,187,904 B1 2/2001 Broekaert et al. .......... 530/324
6,215,048 B1 4/2001 Liang et al. ................ 800/317
2001/0014732 A1 8/2001 Broekaert et al. .......... 530/324

FOREIGN PATENT DOCUMENTS

WO WO 93/05153 A1 3/1993
WO WO 94/16076 A1 7/1994
WO WO 97/21814 A1 6/1997
WO WO 97/21815 A2 6/1997
WO WO 97/37024 A2 10/1997
WO WO 98/00023 A2 1/1998
WO WO 99/02038 A1 1/1999
WO WO 00/11196 A1 3/2000
WO WO 00/68405 A2 11/2000
WO WO 00/78983 A2 12/2000
WO WO 02/063011 A1 8/2002

OTHER PUBLICATIONS

Urwin et al. The Plant Journal (1997), vol. 12(2) pp. 455–461.*

Chih–Ching, C., et al., "Establishment of an Efficient Medium for Anther Culture of Rice Through Comparative Experiments on the Nitrogen Sources" *Sci. Sin. Peking*, 1975, pp. 659–668, vol. 18(5).

Doyle, J., et al., "The Glycosylated Seed Storage Proteins of *Glycine max* and *Phaseolus vulgaris,*" *Journ. of Biol. Chem.*, 1986, pp. 9228–9238, vol. 261(20), The American Society of Biological Chemists, Inc., USA.

Ezaki, B., et al., "Cloning and Sequencing of the cDNAs Induced by Aluminum Treatment and $P_1$ Slarvation in Cultured Tobacco Cells," *Physiologia Plantarum*, 1995, pp. 11–18, vol. 93.

Fromm, M., et al., "Inheritance and Expression of Chimeric Genes in the Progeny of Transgenic Maize Plants," *Bio/Technology*, 1990, pp. 833–839, vol. 8.

Garcia–Olmedo, F., et al., "Plant Defense Peptides," *Biopolymers* (*Peptide Science*), 1998, pp. 479–491, vol. 47, John Wiley & Sons, Inc, USA.

Gritz, L., and J. Davies, "Plasmid–Encoded Hygromycin B Resistance: The Sequence of Hygromycin B Phosphotransferase Gene and Its Expression in *Escherichia coli* and *Saccharomyas cerevisiae*," Gene, 1983, pp. 179–188, vol. 25, Elsevier Science Publishers.

Higgins, D., and P. Sharp, "Fast and Sensitive Multiple Sequence Alignments on a Microcomputer," *Cablos Conura.*, 1989, pp. 151–153, vol. 5(2).

Jia–Qt, C., et al., "The Important Role of Historical Flood Data in the Estimation of Spillway Design Floods," *Sci. Sin. Peking*, 1975, pp. 657–658, vol. 18(5).

Klein, T., et al., "High–Velocity Microprojectiles for Delivering Nucleic Acids into Living Cells," *Nature*, 1987, pp. 70–73, vol. 327.

Maitra, N., et al., "Characterization of a Drought–Induced Soybean cDNA Encoding a Plant Defensin," *Plant Phys.*, 1998, p. 1536, vol. 118.

(List continued on next page.)

*Primary Examiner*—Medina A. Ibrahim
(74) *Attorney, Agent, or Firm*—Alston & Bird LLP

(57) ABSTRACT

This invention relates to isolated nucleic acids encoding plant defensins. The invention also relates to the construction of a chimeric gene encoding all or a portion of the plant defensin, in sense or antisense orientation, wherein expression of the chimeric gene results in production of altered levels of plant defensins in a transformed host cell.

41 Claims, 7 Drawing Sheets

OTHER PUBLICATIONS

Figure 3:
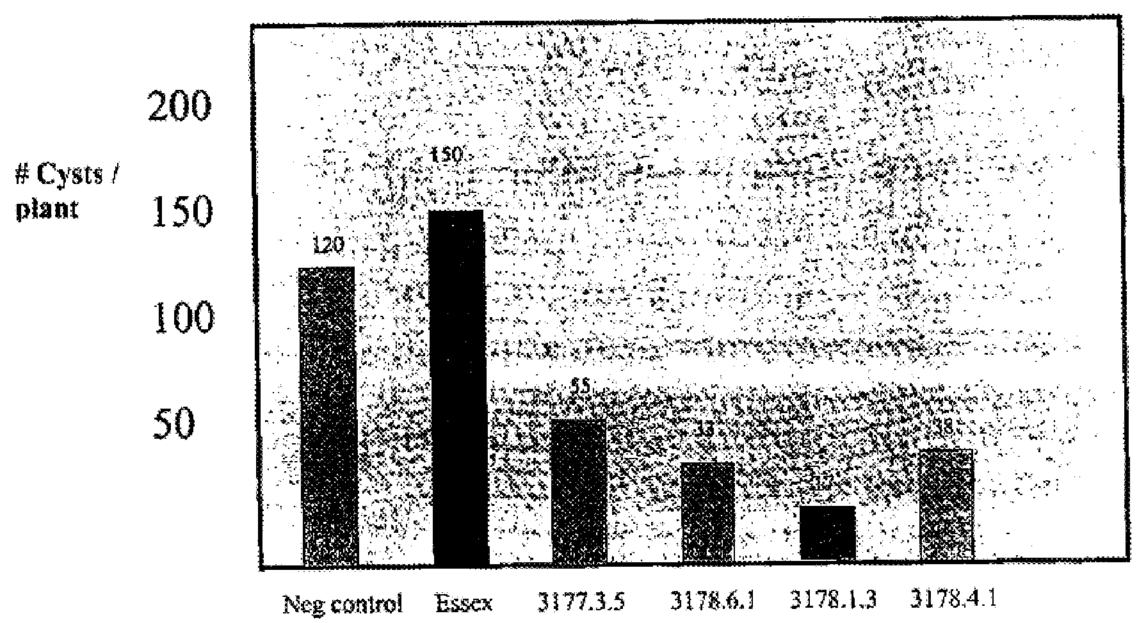

Manners, J., et al., "The Promoter of the Plant Defensin Gene *PDF1.2* from *Arabidopsis* is Systemically Activated by Fungal Pathogens and Responds to Methyl Jasmonate But Not to Sallcylic Acid," *Plant Mol. Biol.*, 1998, pp. 1071–1080, vol. 38, Kluwer Academic Publishers, Netherlands.

Odell, J., et al., "Identification of DNA Sequences Required for Activity of the Cauliflower Mosnic Vinus 35S Promoter," *Nature*, 1985, pp. 810–812, vol. 313.

Osborn, R., et al., "Isolation and Characterisation of Plant Defensins from Seeds of Asteraccae, Fabaccae, Hippocastannceae and Saxifragaceae," FEBS Letters, 1995, pp. 257–262. vol. 368, FEBS.

Rosenberg, A., et al., "Vectors for Selective Expression of Cloned DNAs by T7 RNA Polymerase," *Gene*, 1987, pp. 125–135, vol. 56, Elsevier Science Publishers, BV.

Studier, F., and B. Moffatt, "Use of Bacteriophage T7 RNA Polymerase to Direct Selective High–Level Expression of Cloned Genes," *J. Mol. Biol.*, 1986, pp. 113–130, vol. 189.

Terras, F., et al., "Evidence that the Role of Plant Defensins in Radish Defense Responses is Independent of Salicylic Acid," *Planta*, 1998, pp. 117–124, vol. 206, Springer–Verlag.

Terras, F., et al., "Small Cysteine–Rich Antifungal Proteins from Radish: Their Role in Host Defense," *The Plant Cell*, May 1995, pp. 573–588, vol. 7, American Society of Plant Physiologies, USA.

Thevissen, K., et al., "Fungal Membrane Responses Induced by Plant Defensins and Thionins," *J. of Biol. Chem.*, 1996, pp. 15018–15025, vol. 271(25), The American Society of Biochemistry and Molecular Biology, Inc., USA.

Yamada, S., et al., "cDNA Cloning of$\gamma$–Thionin from *Nicotiana excelsion,"* *Plant Phys.*, 1997, p. 314, vol. 115.

GenBank Report for Accession No. BAA06149, Direct Submission on Mar. 28, 1994.

GenBank Report for Accession No. S66221, Direct Submission on Mar. 19, 1997.

De Lucca, A., et al., "Fungicidal and Binding Properties of the Natural Peptides Cecropin B and Dermaseprin," *Medical Mycology*, Oct. 1998, pp. 291–298, vol. 36(5), ISHAM.

De Lucca, A., et al., "Fungicidal Properties, Sterol Binding, and Proteolytic Resistance of the Synthetic Peptide D4E1," *Can. J. Microbiol.*, 1998, pp. 514–520, vol. 44, NRC Canada.

Thomma, B., et al., "Plant Defensins," *Planta*, 2002, pp. 193–202, vol. 216.

Urwin, P.E., et al., "Resistance to Both Cyst and Root–knot Nematodes Conferred by Transgenic *Arabidopsis* Expressing a Modified Plant Cystatin," *The Plant Journal*, 1997, pp. 455–461, vol. 12(2).

* cited by examiner

```
              *       ***                           *
SEQ ID NO:04  MMKRSVAL---STCTLILFVL--------------TISEIATVRSA--------------
SEQ ID NO:08  MAKPATILAILFASFVILASFESSMGARSTEEKPEAVPEAEQTVGDQVNAEADTVIDPDQ
SEQ ID NO:12  MTKTSVAF---FA-FLLLLVL--------------AISEIGSVKGE--------------
SEQ ID NO:14  MTKTSVAF---FA-FLLLLVL--------------AISEIGSVKGE--------------
SEQ ID NO:16  MTKTSVAF---FA-FLLLLVL--------------AISEIGSVKGE--------------
SEQ ID NO:18  MAKTSVAF---FA-FLLLLVL--------------AISEIGSVKGE--------------
SEQ ID NO:20  MAKTSVAF---FA-FLLLLVL--------------AISEIGSVKGE--------------
SEQ ID NO:22  MAKTSVAF---FA-FLLLLVL--------------AISEIGSVKGE--------------
SEQ ID NO:24  MAKTSVAF---FA-FLLLLVL--------------AISEIGSVKGE--------------
SEQ ID NO:28  MSNK-VFLAILF-CFLLI--------------------------------ASNEMQGGEA
SEQ ID NO:33  ----------------------------------------------E-------------
              1                                                          60

                *   * **** * **  *  ***  * *  ****       ***** *  * * *  *
SEQ ID NO:04  -LCEKASKTWSGNCGNTGHCDDQCKSWETAAHGACHVRGGKHMCFCYFNCKEAEKLAQDK
SEQ ID NO:08  RLCERASLTWSGNCGNTAHCDNQCRSWEHAQHGACHVRGGKHMCFCYFNC----------
SEQ ID NO:12  -LCEKASKTWSGNCGNTRHCDDQCKSWEGAAHGACHVRGGKHMCFCYFQCPKAEKMAQDK
SEQ ID NO:14  -LCEKASKTWSGNCGNTRHCDDQCKSWEGAAHGACHVRGGKHMCFCYFQCPKAEKMAQDK
SEQ ID NO:16  -LCEKASKTWSGNCGNTRHCDDQCKSWEGAAHGACHVRGGKHMCFCYFQCPKAXKMAXG-
SEQ ID NO:18  -LCEKASKTWSGNCGNTRHCDDQCKSWEGAAHGACHVRGGKHMCFCYFQCPKAEKMAQDK
SEQ ID NO:20  -LCEKASKTWSGNCGNTRHCDDQCKSWEGAAHGACHVRGGKHMCFCYFQCPKAEKMAQDK
SEQ ID NO:22  -LCEKASKTWSGNCGNTRHCDDQCKSWEGAAHGACHVRGGKHMCFCYFQCPKAEKMAQDK
SEQ ID NO:24  -LCEKASKTWSGNCGNTRHCDDQCKSWEGAAHGACHVRGGKHMCFCYFQCPKAEKMAQDK
SEQ ID NO:28  KVCQRRSKTWSGPCINTGNCSRQCKNQEDARFGACHRSGIGFACFCYFNC----------
SEQ ID NO:33  -LCEKASKTWSGNCGNTGHCDNQCKSWEGAAHGACHVRNGKHMCFCYFNC----------
              61                                                        120
```

FIGURE 1A

```
               * **
SEQ ID NO:04   LNAEKFGRDDVKVVSDIKNP--------
SEQ ID NO:08   ----------------------------
SEQ ID NO:12   LRAEELAKEKIEAEKEPAKP--------
SEQ ID NO:14   LRAEELAKEKIEAEKEPTKP--------
SEQ ID NO:16   ----------------------------
SEQ ID NO:18   LRAEELAKEKIEAEKEPXKP--------
SEQ ID NO:20   LRAEELAKEKIEVEKEPTKP--------
SEQ ID NO:22   LRAEELAKEKIEAEKEXSQTLSSKMLCL
SEQ ID NO:24   LRAEELAKEKIEVEKEPAKP--------
SEQ ID NO:28   ----------------------------
SEQ ID NO:33   ----------------------------
              121                       148
```

FIGURE 1B

```
SEQ ID NO: 33   ~~~~~~~~~~ ~~~~~~~~~~ ~~~~~~~~~~ ~~~~~~~~~~ ~~~~~~~~~~
SEQ ID NO: 49   ~~~~~~~~~~ ~~~~~~~~~~ ~~~~~~~~~~ MVQKSIVFSA FLLILF...I
SEQ ID NO: 32   ~~~~~~~~~~ ~~~~~~~~~~ ~~~~~~~~~~ MVQKSIVFSA FLLILFVLTI
SEQ ID NO: 47   ~~~~~~~~~~ ~~~~~~~~~~ ~~~~~~~~~~ MAKNSVVFYA FLLLLFVLAI
SEQ ID NO: 30   MAKPATILAI LFASFVILAS FESSMGARST EEKPEAVPEA EQTVGDQVNA
Consensu        ~~~~~~~~~~ ~~~~~~~~~~ ~~~~~~~~~~ ~~~~~~~~~~ ~~~~~~~~~~

SEQ ID NO: 33   --------E. .LCEKASKTW SGNCGNTGHC DNQCKSWEGA AHGACHVRNG
SEQ ID NO: 49   SEISSVRAE. .LCEKASKTW SGNCGNTGHC DNQCKSWEGA AHGACHVRGG
SEQ ID NO: 32   SEISSVRAE. .LCERASKTW SGNCGNTGHC DNQCKSWEGA AHGACHVRGG
SEQ ID NO: 47   SEIGSVKGE. .LCEKASKTW SGKCGNTRHC DDQCKSWEGA AHGACHVRGG
SEQ ID NO: 30   EADTVIDPDQ RLCERASLTW SGNCGNTAHC DNQCRSWEHA QHGACHVRGG
Consensus       ~~~~~~~~~~ -LCE-AS-TW SG-CGNT-HC D-QC-SWE-A -HGACHVR-G

SEQ ID NO: 33   KHMCFCYFNC ~~~~~~~~~~ ~~~~~~~~~~ ~~~~~~~~~~ ~~~~~~~~~~
SEQ ID NO: 49   KHMCFCYFNC KKAEKLAQDK LKAEELAKDK LKADKFDHDA KEVVPNVEHP*
SEQ ID NO: 32   KHMCFCYFNC KKAEKLAQDK LKAEELAKDK LKADKFDHDA KEVVPNVEHP*
SEQ ID NO: 47   KHMCFCYFNC SKAQKLAQDK LIAEELAKEK IEAEKVIAKP *~~~~~~~~~~
SEQ ID NO: 30   KHMCFCYFNC *~~~~~~~~~ ~~~~~~~~~~ ~~~~~~~~~~ ~~~~~~~~~~
Consensus       KHMCFCYFNC ~~~~~~~~~~ ~~~~~~~~~~ ~~~~~~~~~~ ~~~~~~~~~~
```

Figure 2 shows the amino acid alignment of selected proteins of the invention. The consensus sequence is represented in the sequence listing by SEQ ID NO: 51.

FIGURE 2

SEQUENCE LISTING

```
<160> NUMBER OF SEQ ID NOS: 51
<210> SEQ ID NO 1
<211> LENGTH: 503
<212> TYPE: DNA
<213> ORGANISM: Dimorphotheca sinuata
<220> FEATURE:
<221> NAME/KEY: misc_feature
<222> LOCATION: 321, 349, 416, 458, 474, 479, 482, 502
<223> OTHER INFORMATION: n = A,T,C or G

<400> SEQUENCE: 1

ccttatcgtg attcaaaatg atgaaaagat cggttgctct ttccacatgc actttaattc     60

ttttcgtgct cactatctca gaaatcgcga ctgtgagaag tgcactatgt gagaaagcta    120

gcaagacatg gtcaggcaac tgtggcaaca cgggacactg tgacgaccag tgtaagtcgt    180

gggagactgc agcccatggt gcgtgtcatg tgcgtggtgg gaaacacatg tgcttctgct    240

acttcaattg taaagaagcc gaaaagcttg cccaagacaa gctcaacgct gaaaaattcg    300

gccgtgatga cgttaaagta ntgtcggata tcaagaatcc atgaaaggnt tagtttcctt    360
```

-continued

```
agacacgaaa aatctcagat taaaataaat aatagaataa ataaattatt aaatanaaat    420

tgcttgttga ttgtcaaaaa aaaaaaaaaa aaaactcnag gggggggccg gtanccaant    480

cnccctaaaa ggagtcgtat tna                                            503


<210> SEQ ID NO 2
<211> LENGTH: 49
<212> TYPE: PRT
<213> ORGANISM: Dimorphotheca sinuata

<400> SEQUENCE: 2

Leu Cys Glu Lys Ala Ser Lys Thr Trp Ser Gly Asn Cys Gly Asn Thr
 1               5                  10                  15

Gly His Cys Asp Asp Gln Cys Lys Ser Trp Glu Thr Ala Ala His Gly
            20                  25                  30

Ala Cys His Val Arg Gly Gly Lys His Met Cys Phe Cys Tyr Phe Asn
        35                  40                  45

Cys


<210> SEQ ID NO 3
<211> LENGTH: 460
<212> TYPE: DNA
<213> ORGANISM: Dimorphotheca sinuata

<400> SEQUENCE: 3

gcacgagcct tatcgtgatt caaaatgatg aaaagatcgg ttgctctttc cacatgcact     60

ttaattcttt tcgtgctcac tatctcagaa atcgcgactg tgagaagtgc actatgtgag    120

aaagctagca agacatggtc aggcaactgt ggcaacacgg gacactgtga cgaccagtgt    180

aagtcgtggg agactgcagc ccatggtgcg tgtcatgtgc gtggtgggaa acacatgtgc    240

ttctgctact tcaattgtaa agaagccgaa aagcttgccc aagacaagct caacgctgaa    300

aaattcggcc gtgatgacgt taaagtagtg tcggatatca agaatccatg aaaggattag    360

tttccttaga cacgaaaaat ctcagattaa aataaataat agaataaata aattattaaa    420

tagaaattgc ttgttgattg tcaaaaaaaa aaaaaaaaaa                          460


<210> SEQ ID NO 4
<211> LENGTH: 108
<212> TYPE: PRT
<213> ORGANISM: Dimorphotheca sinuata

<400> SEQUENCE: 4

Met Met Lys Arg Ser Val Ala Leu Ser Thr Cys Thr Leu Ile Leu Phe
 1               5                  10                  15

Val Leu Thr Ile Ser Glu Ile Ala Thr Val Arg Ser Ala Leu Cys Glu
            20                  25                  30

Lys Ala Ser Lys Thr Trp Ser Gly Asn Cys Gly Asn Thr Gly His Cys
        35                  40                  45

Asp Asp Gln Cys Lys Ser Trp Glu Thr Ala Ala His Gly Ala Cys His
    50                  55                  60

Val Arg Gly Gly Lys His Met Cys Phe Cys Tyr Phe Asn Cys Lys Glu
65                  70                  75                  80

Ala Glu Lys Leu Ala Gln Asp Lys Leu Asn Ala Glu Lys Phe Gly Arg
                85                  90                  95

Asp Asp Val Lys Val Val Ser Asp Ile Lys Asn Pro
            100                 105
```

<210> SEQ ID NO 5
<211> LENGTH: 501
<212> TYPE: DNA
<213> ORGANISM: Picramnia pentandra
<220> FEATURE:
<221> NAME/KEY: misc_feature
<222> LOCATION: 10, 14, 215, 240, 283, 311, 356, 407, 444, 451, 455, 484, 501
<223> OTHER INFORMATION: n = A,T,C or G

<400> SEQUENCE: 5

```
cagcaaatan caancttaaa ttaaaagcag aaaaatggcc aaaccagcaa ccattcttgc     60

catcctgttt gcctcttttg tcattcttgc ttcgtttgag agttccatgg gagcaagatc    120

tacagaagag aaacccgagg ccgtaccaga ggctgagcag accgtagggg atcaagtcaa    180

tgcagaagct gacacagtta tagacccgga ccaangacta tgtgaaagag caagcttaan    240

atggtcaggc aattgtggca acactgctca ctgtgacaac cantgtaagt catgggagca    300

cgcacaacac ngagcatgtc acgtacgagg tggaaaacat aagtgcttct gctacntcaa    360

ttgctgatct caaagaaagc accttcccaa tgggtgcaac aagtaanaat gttaaaataa    420

aataatttta gacatcaata cacngtctaa naatncttaa caatccttat ggttaagata    480

cttnagtgct atcagtgaaa n                                              501
```

<210> SEQ ID NO 6
<211> LENGTH: 49
<212> TYPE: PRT
<213> ORGANISM: Picramnia pentandra
<220> FEATURE:
<221> NAME/KEY: VARIANT
<222> LOCATION: 8, 22, 32, 47
<223> OTHER INFORMATION: Xaa = Any Amino Acid

<400> SEQUENCE: 6

```
Leu Cys Glu Arg Ala Ser Leu Xaa Trp Ser Gly Asn Cys Gly Asn Thr
 1               5                  10                  15

Ala His Cys Asp Asn Xaa Cys Lys Ser Trp Glu His Ala Gln His Xaa
            20                  25                  30

Ala Cys His Val Arg Gly Gly Lys His Lys Cys Phe Cys Tyr Xaa Asn
        35                  40                  45

Cys
```

<210> SEQ ID NO 7
<211> LENGTH: 658
<212> TYPE: DNA
<213> ORGANISM: Picramnia pentandra

<400> SEQUENCE: 7

```
gcacgagcag caaatagcaa acttaaatta aaagcagaaa aatggccaaa ccagcaacca     60

ttcttgccat cctgtttgcc tcttttgtca ttcttgcttc gtttgagagt tccatgggag    120

caagatctac agaagagaaa cccgaggccg taccagaggc tgagcagacc gtaggggatc    180

aagtcaatgc agaagctgac acagttatag acccggacca aagactatgt gaaagagcaa    240

gcttaacatg gtcaggcaat tgtggcaaca ctgctcactg tgacaaccag tgtaggtcat    300

gggagcacgc acaacacgga gcatgtcacg tacgaggtgg aaaacatatg tgcttctgct    360

acttcaattg ctgatctcaa agaaagcatc gttcgccaat ggttgcaaca agtaataatg    420

ttaaaaataa aaataagtat agaccatcaa tacacggtct aagaattctt aacaatcctt    480

attgttaaga ttacgttaag tgctatcagt gaaactagga ttgtcaccca actatgttcc    540
```

```
agcaagctgg ctctgttgtt cttattttcc agtggttaat aaaaagattg tccaactctt    600

ttacactaaa aaaaaaaaaa aaaaaaaaaa aaaaaaaaaa aaaaaaaaaa aaaaaaa       658


<210> SEQ ID NO 8
<211> LENGTH: 110
<212> TYPE: PRT
<213> ORGANISM: Picramnia pentandra

<400> SEQUENCE: 8

Met Ala Lys Pro Ala Thr Ile Leu Ala Ile Leu Phe Ala Ser Phe Val
 1               5                  10                  15

Ile Leu Ala Ser Phe Glu Ser Ser Met Gly Ala Arg Ser Thr Glu Glu
            20                  25                  30

Lys Pro Glu Ala Val Pro Glu Ala Glu Gln Thr Val Gly Asp Gln Val
        35                  40                  45

Asn Ala Glu Ala Asp Thr Val Ile Asp Pro Asp Gln Arg Leu Cys Glu
    50                  55                  60

Arg Ala Ser Leu Thr Trp Ser Gly Asn Cys Gly Asn Thr Ala His Cys
65                  70                  75                  80

Asp Asn Gln Cys Arg Ser Trp Glu His Ala Gln His Gly Ala Cys His
                85                  90                  95

Val Arg Gly Gly Lys His Met Cys Phe Cys Tyr Phe Asn Cys
            100                 105                 110


<210> SEQ ID NO 9
<211> LENGTH: 463
<212> TYPE: DNA
<213> ORGANISM: Parthenium argentatum Grey
<220> FEATURE:
<221> NAME/KEY: misc_feature
<222> LOCATION: 413
<223> OTHER INFORMATION: n = A,T,C or G

<400> SEQUENCE: 9

caagtgttct tgagcttcag tgcattgatc caaaatgacc aaaacttcag ttgctttctt     60

tgcatttctt ctgctcctcg ttcttgctat ctcagaaatc ggatcggtga agggagaact    120

atgtgagaag gcaagcaaga catggtctgg aaattgtggt aacacaagac attgtgacga    180

ccaatgcaag tcttgggagg gtgcagccca tggagcttgt catgtgcgcg gtgggaaaca    240

catgtgcttc tgctacttcc agtgccccaa agccgagaag atggcccagg ataaactccg    300

agctgaagag cttgccaagg agaagattga agctgaaaaa gagccaacca aaccttgagt    360

agcaaatgtt atgcttatga ataagagaaa atgctttcta cttacatgtt cancaatttc    420

taaggggtaa tgtttcctgc aattgggatc aattgttatg att                      463


<210> SEQ ID NO 10
<211> LENGTH: 50
<212> TYPE: PRT
<213> ORGANISM: Parthenium argentatum Grey

<400> SEQUENCE: 10

Glu Leu Cys Glu Lys Ala Ser Lys Thr Trp Ser Gly Asn Cys Gly Asn
 1               5                  10                  15

Thr Arg His Cys Asp Asp Gln Cys Lys Ser Trp Glu Gly Ala Ala His
            20                  25                  30

Gly Ala Cys His Val Arg Gly Gly Lys His Met Cys Phe Cys Tyr Phe
        35                  40                  45
```

```
Gln Cys
    50


<210> SEQ ID NO 11
<211> LENGTH: 603
<212> TYPE: DNA
<213> ORGANISM: Parthenium argentatum Grey

<400> SEQUENCE: 11

gcacgagcaa gtgttcttga gcttcagtgc attgatccaa aatgaccaaa acttcagttg     60

ctttctttgc atttcttctg ctcctcgttc ttgctatctc agaaatcgga tcggtgaagg    120

gagaactatg tgagaaggca agcaagacat ggtctggaaa ttgtggtaac acaagacatt    180

gtgacgacca atgcaagtct tgggagggtg cagcccatgg agcttgtcat gtgcgcggtg    240

ggaaacacat gtgcttctgc tacttccagt gccccaaagc cgagaagatg gcccaggata    300

aactccgagc tgaagagctt gccaaggaga agattgaagc tgaaaaagag ccagccaaac    360

cttgagtagc aaatgttatg cttatgaata agagaaaatg ctttctactt acatgttcag    420

cattttctat ggtgtaatgt ttcttgcatt tggaatcaat tgttatgatt ccttgtaaaa    480

tgttctaatg atgtaataag tttcctgcat aaattatgtt gttttaaagc ctgtggaata    540

aaattttatg tgcatgcaaa aaaaaaaaaa aaaaaaaaaa aaaaaaaaaa aaaaaaaaaa    600

aaa                                                                  603


<210> SEQ ID NO 12
<211> LENGTH: 107
<212> TYPE: PRT
<213> ORGANISM: Parthenium argentatum Grey

<400> SEQUENCE: 12

Met Thr Lys Thr Ser Val Ala Phe Phe Ala Phe Leu Leu Leu Leu Val
 1               5                  10                  15

Leu Ala Ile Ser Glu Ile Gly Ser Val Lys Gly Glu Leu Cys Glu Lys
            20                  25                  30

Ala Ser Lys Thr Trp Ser Gly Asn Cys Gly Asn Thr Arg His Cys Asp
        35                  40                  45

Asp Gln Cys Lys Ser Trp Glu Gly Ala Ala His Gly Ala Cys His Val
    50                  55                  60

Arg Gly Gly Lys His Met Cys Phe Cys Tyr Phe Gln Cys Pro Lys Ala
65                  70                  75                  80

Glu Lys Met Ala Gln Asp Lys Leu Arg Ala Glu Glu Leu Ala Lys Glu
                85                  90                  95

Lys Ile Glu Ala Glu Lys Glu Pro Ala Lys Pro
            100                 105


<210> SEQ ID NO 13
<211> LENGTH: 457
<212> TYPE: DNA
<213> ORGANISM: Parthenium argentatum Grey
<220> FEATURE:
<221> NAME/KEY: misc_feature
<222> LOCATION: 424, 436
<223> OTHER INFORMATION: n = A,T,C or G

<400> SEQUENCE: 13

gtgttcttga gcttcagtgc attgatccaa aatgaccaaa acttcagttg ctttctttgc     60

atttcttctg ctcctcgttc ttgctatctc agaaatcgga tcggtgaagg gagaactatg    120

tgagaaggca agcaagacat ggtctggaaa ttgtggtaac acaagacatt gtgacgacca    180
```

-continued

```
atgcaagtct tgggagggtg cagcccatgg agcttgtcat gtgcgcggtg ggaaacacat    240

gtgcttctgc tacttccagt gccccaaagc cgagaagatg gcccaggata aactccgagc    300

tgaagagctt gccaaggaga agattgaagc tgaaaaagag ccaaccaaac cttgagtagc    360

aaatgttatg cttatgaata aaagaaaatg ctttctactt acatgttcaa caatttccta    420

tggngtaatg tttccntgca tttgggaatc aaattgg                             457
```

<210> SEQ ID NO 14
<211> LENGTH: 107
<212> TYPE: PRT
<213> ORGANISM: Parthenium argentatum Grey

<400> SEQUENCE: 14

```
Met Thr Lys Thr Ser Val Ala Phe Phe Ala Phe Leu Leu Leu Leu Val
 1               5                  10                  15

Leu Ala Ile Ser Glu Ile Gly Ser Val Lys Gly Glu Leu Cys Glu Lys
            20                  25                  30

Ala Ser Lys Thr Trp Ser Gly Asn Cys Gly Asn Thr Arg His Cys Asp
        35                  40                  45

Asp Gln Cys Lys Ser Trp Glu Gly Ala Ala His Gly Ala Cys His Val
    50                  55                  60

Arg Gly Gly Lys His Met Cys Phe Cys Tyr Phe Gln Cys Pro Lys Ala
65                  70                  75                  80

Glu Lys Met Ala Gln Asp Lys Leu Arg Ala Glu Glu Leu Ala Lys Glu
                85                  90                  95

Lys Ile Glu Ala Glu Lys Glu Pro Thr Lys Pro
            100                 105
```

<210> SEQ ID NO 15
<211> LENGTH: 439
<212> TYPE: DNA
<213> ORGANISM: Parthenium argentatum Grey
<220> FEATURE:
<221> NAME/KEY: misc_feature
<222> LOCATION: 276, 288, 349, 438
<223> OTHER INFORMATION: n = A,T,C or G

<400> SEQUENCE: 15

```
aagtgttctt gagcttcagt gcattgatcc aaaatgacca aaacttcagt tgctttcttt     60

gcatttcttc tgctcctcgt tcttgctatc tcagaaatcg gatcggtgaa gggagaacta    120

tgtgagaagg caagcaagac atggtctgga aattgtggta acacaagaca ttgtgacgac    180

caatgcaagt cttgggaggg tgcagcccat ggagcttgtc atgtgcgcgg tgggaaacac    240

atgtgcttct gctacttcca gtgccccaaa gccganaaga tggcccangg ataaactccg    300

agctgaagaa gcttgccaag gagaagattg aagctgaaaa agagccagnc aaaccttgag    360

taagcaaatg tttatgctta tgaaataaag aagaaaatgc ttttctactt tacatgttca    420

gcaatttcct aagggggna                                                 439
```

<210> SEQ ID NO 16
<211> LENGTH: 86
<212> TYPE: PRT
<213> ORGANISM: Parthenium argentatum Grey
<220> FEATURE:
<221> NAME/KEY: VARIANT
<222> LOCATION: 81, 85
<223> OTHER INFORMATION: Xaa = Any Amino Acid

<400> SEQUENCE: 16

-continued

```
Met Thr Lys Thr Ser Val Ala Phe Phe Ala Phe Leu Leu Leu Leu Val
 1               5                  10                  15

Leu Ala Ile Ser Glu Ile Gly Ser Val Lys Gly Glu Leu Cys Glu Lys
            20                  25                  30

Ala Ser Lys Thr Trp Ser Gly Asn Cys Gly Asn Thr Arg His Cys Asp
        35                  40                  45

Asp Gln Cys Lys Ser Trp Glu Gly Ala Ala His Gly Ala Cys His Val
    50                  55                  60

Arg Gly Gly Lys His Met Cys Phe Cys Tyr Phe Gln Cys Pro Lys Ala
65                  70                  75                  80

Xaa Lys Met Ala Xaa Gly
                85


<210> SEQ ID NO 17
<211> LENGTH: 460
<212> TYPE: DNA
<213> ORGANISM: Parthenium argentatum Grey
<220> FEATURE:
<221> NAME/KEY: misc_feature
<222> LOCATION: 342
<223> OTHER INFORMATION: n = A,T,C or G

<400> SEQUENCE: 17

gtttttgagc ttcagtgcat tgatccaaaa tggccaaaac ttcagttgct ttctttgcat     60

ttcttctgct cctcgttctt gctatctcag aaatcggatc ggtgaaggga gaactatgtg    120

agaaggcaag caagacatgg tctggaaatt gtggtaacac aagacactgt gacgaccaat    180

gcaagtcttg ggagggtgca gcccatggag cttgtcatgt gcgcggtggg aaacacatgt    240

gcttctgcta cttccagtgc cccaaagccg agaagatggc ccaggataaa ctccgagctg    300

aagagcttgc caaggagaag attgaagctg aaaaagagcc anccaaacct tgagtagcaa    360

atgttatgct tatgaataaa aagaaaatgc tttctactta catctttagc aatttctaag    420

gggtaatgtt tcctgcattt gggatcaaat tgttatgatc                          460


<210> SEQ ID NO 18
<211> LENGTH: 107
<212> TYPE: PRT
<213> ORGANISM: Parthenium argentatum Grey
<220> FEATURE:
<221> NAME/KEY: VARIANT
<222> LOCATION: 105
<223> OTHER INFORMATION: Xaa = Any Amino Acid

<400> SEQUENCE: 18

Met Ala Lys Thr Ser Val Ala Phe Phe Ala Phe Leu Leu Leu Leu Val
 1               5                  10                  15

Leu Ala Ile Ser Glu Ile Gly Ser Val Lys Gly Glu Leu Cys Glu Lys
            20                  25                  30

Ala Ser Lys Thr Trp Ser Gly Asn Cys Gly Asn Thr Arg His Cys Asp
        35                  40                  45

Asp Gln Cys Lys Ser Trp Glu Gly Ala Ala His Gly Ala Cys His Val
    50                  55                  60

Arg Gly Gly Lys His Met Cys Phe Cys Tyr Phe Gln Cys Pro Lys Ala
65                  70                  75                  80

Glu Lys Met Ala Gln Asp Lys Leu Arg Ala Glu Glu Leu Ala Lys Glu
                85                  90                  95

Lys Ile Glu Ala Glu Lys Glu Pro Xaa Lys Pro
            100                 105
```

<210> SEQ ID NO 19
<211> LENGTH: 464
<212> TYPE: DNA
<213> ORGANISM: Parthenium argentatum Grey
<220> FEATURE:
<221> NAME/KEY: misc_feature
<222> LOCATION: 445, 452
<223> OTHER INFORMATION: n = A,T,C or G

<400> SEQUENCE: 19

```
caagtgttct tgagcttcag tgcattgatc caaaatggcc aaaacttcag ttgctttctt     60

tgcatttctt ctgctcctcg ttcttgctat ctcagaaatc ggatcggtga agggagaact    120

atgtgagaag gcaagcaaga catggtctgg aaattgtggt aacacaagac actgtgacga    180

ccaatgcaag tcttgggagg gtgcagccca tggagcttgt catgtgcgcg gtgggaaaca    240

catgtgcttc tgctacttcc agtgccccaa agccgagaag atggcccagg ataaactccg    300

agctgaagag cttgccaagg agaagattga agttgaaaaa gagccaacca aaccttgagt    360

agcaaatgtt atgtttatga ataaagagaa aatgctttct acttacatgt tcaacaattt    420

ccaaggggga aatgtttccc tgcanttgga ancaattgtt atga                     464
```

<210> SEQ ID NO 20
<211> LENGTH: 107
<212> TYPE: PRT
<213> ORGANISM: Parthenium argentatum Grey

<400> SEQUENCE: 20

```
Met Ala Lys Thr Ser Val Ala Phe Phe Ala Phe Leu Leu Leu Leu Val
 1               5                  10                  15

Leu Ala Ile Ser Glu Ile Gly Ser Val Lys Gly Glu Leu Cys Glu Lys
            20                  25                  30

Ala Ser Lys Thr Trp Ser Gly Asn Cys Gly Asn Thr Arg His Cys Asp
        35                  40                  45

Asp Gln Cys Lys Ser Trp Glu Gly Ala Ala His Gly Ala Cys His Val
    50                  55                  60

Arg Gly Gly Lys His Met Cys Phe Cys Tyr Phe Gln Cys Pro Lys Ala
65                  70                  75                  80

Glu Lys Met Ala Gln Asp Lys Leu Arg Ala Glu Glu Leu Ala Lys Glu
                85                  90                  95

Lys Ile Glu Val Glu Lys Glu Pro Thr Lys Pro
            100                 105
```

<210> SEQ ID NO 21
<211> LENGTH: 458
<212> TYPE: DNA
<213> ORGANISM: Parthenium argentatum Grey
<220> FEATURE:
<221> NAME/KEY: misc_feature
<222> LOCATION: 322, 375, 402, 452
<223> OTHER INFORMATION: n = A,T,C or G

<400> SEQUENCE: 21

```
cattgatcca aaatggccaa aacttcagtt gctttctttg catttcttct gctcctcgtt     60

cttgctatct cagaaatcgg atcggtgaag ggagaactat gtgagaaggc aagcaagaca    120

tggtctggaa attgtggtaa cacaagacac tgtgacgacc aatgcaagtc ttgggagggt    180

gcagcccatg gagcttgtca tgtgcgcggt gggaaacaca tgtgcttctg ctacttccag    240

tgccccaaag ccgagaagat ggcccaggat aaactccgag ctgaagagct tgccaaggag    300
```

```
aagattgaag ctgaaaaaga gncaagccaa accttgagta gcaaaatgtt atgcttatga    360

ataagagaaa atgcnttcta cttaaatctt taacaatttt cnaaggggta atgtttcctg    420

catttggaaa caattgttat gattcccttg tnaaaagg                            458
```

<210> SEQ ID NO 22
<211> LENGTH: 115
<212> TYPE: PRT
<213> ORGANISM: Parthenium argentatum Grey
<220> FEATURE:
<221> NAME/KEY: VARIANT
<222> LOCATION: 104
<223> OTHER INFORMATION: Xaa = Any Amino Acid

<400> SEQUENCE: 22

```
Met Ala Lys Thr Ser Val Ala Phe Phe Ala Phe Leu Leu Leu Leu Val
 1               5                  10                  15

Leu Ala Ile Ser Glu Ile Gly Ser Val Lys Gly Glu Leu Cys Glu Lys
            20                  25                  30

Ala Ser Lys Thr Trp Ser Gly Asn Cys Gly Asn Thr Arg His Cys Asp
        35                  40                  45

Asp Gln Cys Lys Ser Trp Glu Gly Ala Ala His Gly Ala Cys His Val
    50                  55                  60

Arg Gly Gly Lys His Met Cys Phe Cys Tyr Phe Gln Cys Pro Lys Ala
65                  70                  75                  80

Glu Lys Met Ala Gln Asp Lys Leu Arg Ala Glu Glu Leu Ala Lys Glu
                85                  90                  95

Lys Ile Glu Ala Glu Lys Glu Xaa Ser Gln Thr Leu Ser Ser Lys Met
            100                 105                 110

Leu Cys Leu
        115
```

<210> SEQ ID NO 23
<211> LENGTH: 472
<212> TYPE: DNA
<213> ORGANISM: Parthenium argentatum Grey
<220> FEATURE:
<221> NAME/KEY: misc_feature
<222> LOCATION: 368
<223> OTHER INFORMATION: n = A,T,C or G

<400> SEQUENCE: 23

```
cttgagcttc agtgcattga tccaaaatgg ccaaaacttc agttgctttc tttgcatttc     60

ttctgctcct cgttcttgct atctcagaaa tcggatcggt gaagggagaa ctatgtgaga    120

aggcaagcaa gacatggtct ggaaattgtg gtaacacaag acactgtgac gaccaatgca    180

agtcttggga gggtgcagcc catggagctt gtcatgtgcg cggtgggaaa cacatgtgct    240

tctgctactt ccagtgcccc aaagccgaga agatggccca ggataaactc cgagctgaag    300

agcttgccaa ggagaagatt gaagttgaaa aagagccagc caaaccttga gtagcaaatg    360

ttatgttnat gaataaagag aaaatgcttt ctacttacat gttcaacatt ttctatgggg    420

taatgtttct tgcatttggg aatcaattgt tatgattcct tggtaaaatg tt            472
```

<210> SEQ ID NO 24
<211> LENGTH: 107
<212> TYPE: PRT
<213> ORGANISM: Parthenium argentatum Grey

<400> SEQUENCE: 24

-continued

```
Met Ala Lys Thr Ser Val Ala Phe Phe Ala Phe Leu Leu Leu Leu Val
 1               5                  10                  15

Leu Ala Ile Ser Glu Ile Gly Ser Val Lys Gly Glu Leu Cys Glu Lys
            20                  25                  30

Ala Ser Lys Thr Trp Ser Gly Asn Cys Gly Asn Thr Arg His Cys Asp
        35                  40                  45

Asp Gln Cys Lys Ser Trp Glu Gly Ala Ala His Gly Ala Cys His Val
    50                  55                  60

Arg Gly Gly Lys His Met Cys Phe Cys Tyr Phe Gln Cys Pro Lys Ala
65                  70                  75                  80

Glu Lys Met Ala Gln Asp Lys Leu Arg Ala Glu Glu Leu Ala Lys Glu
                85                  90                  95

Lys Ile Glu Val Glu Lys Glu Pro Ala Lys Pro
            100                 105


<210> SEQ ID NO 25
<211> LENGTH: 499
<212> TYPE: DNA
<213> ORGANISM: Nicotiana benthamiana
<220> FEATURE:
<221> NAME/KEY: misc_feature
<222> LOCATION: 451, 456
<223> OTHER INFORMATION: n = A,T,C or G

<400> SEQUENCE: 25

gagaagtagc ataaatttct aaatccatat tcatcatgag caacaaagtc tttctagcca     60

tcttgttttg cttcctcctc attgcatcca atgagatgca aggaggagag gcgaaagttt    120

gccaaaggcg aagcaagaca tggtcggggc cttgtattaa cacaggcaac tgcagccgtc    180

aatgcaagaa tcaagaggat gctcgctttg gtgcttgtca cagaagtggg attggatttg    240

cttgcttctg ctatttcaac tgctaaacga ccaaaaaaag accctatgtg ttttgtctct    300

atttctatga ttgtactatc aaatatgtaa gtgttgtgtg tctgtatgaa taaagggcgt    360

ccaatttact agaattggaa gtagccctag ttgtgttggt gtgtcattcc taaactttgt    420

atttcaatct gggccagctt ttgttggtcc nattantaaa cgacgagtgc gtccacttgt    480

aatcccccca aaaaaaaaa                                                 499


<210> SEQ ID NO 26
<211> LENGTH: 50
<212> TYPE: PRT
<213> ORGANISM: Nicotiana benthamiana

<400> SEQUENCE: 26

Lys Val Cys Gln Arg Arg Ser Lys Thr Trp Ser Gly Pro Cys Ile Asn
 1               5                  10                  15

Thr Gly Asn Cys Ser Arg Gln Cys Lys Asn Gln Glu Asp Ala Arg Phe
            20                  25                  30

Gly Ala Cys His Arg Ser Gly Ile Gly Phe Ala Cys Phe Cys Tyr Phe
        35                  40                  45

Asn Cys
    50


<210> SEQ ID NO 27
<211> LENGTH: 517
<212> TYPE: DNA
<213> ORGANISM: Nicotiana benthamiana

<400> SEQUENCE: 27
```

-continued

```
gcacgaggag aagtagcata aatttctaaa tccatattca tcatgagcaa caaagtcttt      60

ctagccatct tgttttgctt cctcctcatt gcatccaatg agatgcaagg aggagaggcg     120

aaagtttgcc aaaggcgaag caagacatgg tcggggcctt gtattaacac aggcaactgc     180

agccgtcaat gcaagaatca agaggatgct cgctttggtg cttgtcacag aagtgggatt     240

ggatttgctt gcttctgcta tttcaactgc taaacgacca aaaaaagacc ctatgtgttt     300

tgtctctatt tctatgattg tactatcaaa tatgtaagtg ttgtgtgtct gtatgaataa     360

agggcgtcca atttactaga attggaagta gccctagttg tgttggtgtg tcattcctaa     420

actttgtatt tcaatctggc cagcttttgt tggtctatta ttaaacgacg agtgcgtcca     480

cttgttattc cctccaaaaa aaaaaaaaaa aaaaaaa                              517


<210> SEQ ID NO 28
<211> LENGTH: 76
<212> TYPE: PRT
<213> ORGANISM: Nicotiana benthamiana

<400> SEQUENCE: 28

Met Ser Asn Lys Val Phe Leu Ala Ile Leu Phe Cys Phe Leu Leu Ile
 1               5                  10                  15

Ala Ser Asn Glu Met Gln Gly Gly Glu Ala Lys Val Cys Gln Arg Arg
            20                  25                  30

Ser Lys Thr Trp Ser Gly Pro Cys Ile Asn Thr Gly Asn Cys Ser Arg
        35                  40                  45

Gln Cys Lys Asn Gln Glu Asp Ala Arg Phe Gly Ala Cys His Arg Ser
    50                  55                  60

Gly Ile Gly Phe Ala Cys Phe Cys Tyr Phe Asn Cys
65                  70                  75


<210> SEQ ID NO 29
<211> LENGTH: 610
<212> TYPE: DNA
<213> ORGANISM: Picramnia pentandra

<400> SEQUENCE: 29

gcacgagaaa tagcaaactt aaattaaaag cagaaaaatg gccaagccag caaccattct      60

tgccatcctg tttgcctctt ttgtcattct tgcttcgttt gagagttcca tgggagcaag     120

atctacagaa gagaaacccg aggccgtacc agaggctgag cagaccgtag gggatcaagt     180

caatgcagaa gctgacacag ttatagaccc ggaccaaaga ctatgtgaaa gagcaagctt     240

aacatggtca ggcaattgtg gcaacactgc tcactgtgac aaccagtgta ggtcatggga     300

gcacgcacaa cacggagcat gtcacgtacg aggtggaaaa catatgtgct tctgctactt     360

caattgctga tctcaaagaa agcatcgttc gccaatggtt gcaacaagta ataatgttaa     420

aaataaaaat aagtatagac catcaataca cggtctaaga attcttaaca atccttattg     480

ttaagattac gttaagtgct atcagtgaaa ctaggattgt cacccaacta tgttccagca     540

agctggctct gttgttctta ttttccagtg gttaataaaa agattgtcca actcttttac     600

actaaaaaaa                                                            610


<210> SEQ ID NO 30
<211> LENGTH: 110
<212> TYPE: PRT
<213> ORGANISM: Picramnia pentandra

<400> SEQUENCE: 30
```

-continued

```
Met Ala Lys Pro Ala Thr Ile Leu Ala Ile Leu Phe Ala Ser Phe Val
 1               5                  10                  15

Ile Leu Ala Ser Phe Glu Ser Ser Met Gly Ala Arg Ser Thr Glu Glu
            20                  25                  30

Lys Pro Glu Ala Val Pro Glu Ala Glu Gln Thr Val Gly Asp Gln Val
        35                  40                  45

Asn Ala Glu Ala Asp Thr Val Ile Asp Pro Asp Gln Arg Leu Cys Glu
    50                  55                  60

Arg Ala Ser Leu Thr Trp Ser Gly Asn Cys Gly Asn Thr Ala His Cys
65                  70                  75                  80

Asp Asn Gln Cys Arg Ser Trp Glu His Ala Gln His Gly Ala Cys His
                85                  90                  95

Val Arg Gly Gly Lys His Met Cys Phe Cys Tyr Phe Asn Cys
            100                 105                 110


<210> SEQ ID NO 31
<211> LENGTH: 579
<212> TYPE: DNA
<213> ORGANISM: Vernonia mespilifolia

<400> SEQUENCE: 31

tcttaatcga gcttcattct aattcaaaaa tggtgcaaaa atcgattgtt ttctccgcgt      60

tccttctaat cctctttgtt ctcacgatct cagaaatctc gagtgtgaga gcagagctat     120

gcgagagagc tagcaagaca tggtcaggca actgtggcaa cacaggacat tgtgataatc     180

agtgtaagtc atgggagggt gcagcccatg gagcttgtca tgtgcgtgga gggaaacaca     240

tgtgcttttg ctatttcaat tgtaaaaaag ctgaaaaact cgctcaagat aagttaaaag     300

ctgaagagct tgcaaaagac aaactcaagg cagataagtt tgaccatgat gcaaaagaag     360

tagtaccaaa tgtcgaacat ccatgaaaga tcggtttccc taaatcaata gtctgtttta     420

ttatgatatg aataaaaaca gaaagtgttg taataatcac atttttagct tctttagaga     480

tgcattatgt tgtcaattcg gcaccttctt tgttgttata tgtgtaataa tgtatgatat     540

cgaaagccta acgtttccat aaaaaaaaaa aaaaaaaaa                           579


<210> SEQ ID NO 32
<211> LENGTH: 118
<212> TYPE: PRT
<213> ORGANISM: Vernonia mespilifolia

<400> SEQUENCE: 32

Met Val Gln Lys Ser Ile Val Phe Ser Ala Phe Leu Leu Ile Leu Phe
 1               5                  10                  15

Val Leu Thr Ile Ser Glu Ile Ser Ser Val Arg Ala Glu Leu Cys Glu
            20                  25                  30

Arg Ala Ser Lys Thr Trp Ser Gly Asn Cys Gly Asn Thr Gly His Cys
        35                  40                  45

Asp Asn Gln Cys Lys Ser Trp Glu Gly Ala Ala His Gly Ala Cys His
    50                  55                  60

Val Arg Gly Gly Lys His Met Cys Phe Cys Tyr Phe Asn Cys Lys Lys
65                  70                  75                  80

Ala Glu Lys Leu Ala Gln Asp Lys Leu Lys Ala Glu Glu Leu Ala Lys
                85                  90                  95

Asp Lys Leu Lys Ala Asp Lys Phe Asp His Asp Ala Lys Glu Val Val
            100                 105                 110

Pro Asn Val Glu His Pro
```

```
        115


<210> SEQ ID NO 33
<211> LENGTH: 50
<212> TYPE: PRT
<213> ORGANISM: Dahlia merckii

<400> SEQUENCE: 33

Glu Leu Cys Glu Lys Ala Ser Lys Thr Trp Ser Gly Asn Cys Gly Asn
 1               5                  10                  15

Thr Gly His Cys Asp Asn Gln Cys Lys Ser Trp Glu Gly Ala Ala His
            20                  25                  30

Gly Ala Cys His Val Arg Asn Gly Lys His Met Cys Phe Cys Tyr Phe
        35                  40                  45

Asn Cys
    50


<210> SEQ ID NO 34
<211> LENGTH: 156
<212> TYPE: DNA
<213> ORGANISM: Picramnia pentandra
<220> FEATURE:
<221> NAME/KEY: CDS
<222> LOCATION: (1)...(156)
<223> OTHER INFORMATION: Sequence for mature peptide

<400> SEQUENCE: 34

caa aga cta tgt gaa aga gca agc tta aca tgg tca ggc aat tgt ggc       48
Gln Arg Leu Cys Glu Arg Ala Ser Leu Thr Trp Ser Gly Asn Cys Gly
 1               5                  10                  15

aac act gct cac tgt gac aac cag tgt agg tca tgg gag cac gca caa       96
Asn Thr Ala His Cys Asp Asn Gln Cys Arg Ser Trp Glu His Ala Gln
            20                  25                  30

cac gga gca tgt cac gta cga ggt gga aaa cat atg tgc ttc tgc tac      144
His Gly Ala Cys His Val Arg Gly Gly Lys His Met Cys Phe Cys Tyr
        35                  40                  45

ttc aat tgc tga                                                      156
Phe Asn Cys  *
     50


<210> SEQ ID NO 35
<211> LENGTH: 51
<212> TYPE: PRT
<213> ORGANISM: Picramnia pentandra

<400> SEQUENCE: 35

Gln Arg Leu Cys Glu Arg Ala Ser Leu Thr Trp Ser Gly Asn Cys Gly
 1               5                  10                  15

Asn Thr Ala His Cys Asp Asn Gln Cys Arg Ser Trp Glu His Ala Gln
            20                  25                  30

His Gly Ala Cys His Val Arg Gly Gly Lys His Met Cys Phe Cys Tyr
        35                  40                  45

Phe Asn Cys
    50


<210> SEQ ID NO 36
<211> LENGTH: 250
<212> TYPE: DNA
<213> ORGANISM: Artificial Sequence
<220> FEATURE:
<223> OTHER INFORMATION: Synthetic version of Picramnia pentandra mature
      peptide with a barley alpha amylase signal peptide
<220> FEATURE:
```

```
<221> NAME/KEY: CDS
<222> LOCATION: (13)...(240)

<400> SEQUENCE: 36

cccgggctcg ag atg gcc aac aag cat ctt tct ctc agt ctg ttc ttg gtg     51
              Met Ala Asn Lys His Leu Ser Leu Ser Leu Phe Leu Val
               1               5                  10

tta ctc ggt ttg agt gct agc ctt gct tct ggg caa agg ctt tgc gaa       99
Leu Leu Gly Leu Ser Ala Ser Leu Ala Ser Gly Gln Arg Leu Cys Glu
     15                  20                  25

cgc gcg tca cta act tgg tcc ggt aac tgt gga aat acc gcc cac tgc      147
Arg Ala Ser Leu Thr Trp Ser Gly Asn Cys Gly Asn Thr Ala His Cys
 30                  35                  40                  45

gat aat caa tgc cgt tca tgg gag cat gct cag cat gga gca tgt cac      195
Asp Asn Gln Cys Arg Ser Trp Glu His Ala Gln His Gly Ala Cys His
                 50                  55                  60

gtt aga gga ggc aaa cac atg tgc ttc tgt tat ttt aac tgt taa         240
Val Arg Gly Gly Lys His Met Cys Phe Cys Tyr Phe Asn Cys  *
             65                  70                  75

ggtaccatgg                                                           250


<210> SEQ ID NO 37
<211> LENGTH: 75
<212> TYPE: PRT
<213> ORGANISM: Artificial Sequence
<220> FEATURE:
<223> OTHER INFORMATION: Synthetic version of Picramnia pentandra mature
      peptide with a barley alpha amylase signal peptide

<400> SEQUENCE: 37

Met Ala Asn Lys His Leu Ser Leu Ser Leu Phe Leu Val Leu Leu Gly
 1               5                  10                  15

Leu Ser Ala Ser Leu Ala Ser Gly Gln Arg Leu Cys Glu Arg Ala Ser
            20                  25                  30

Leu Thr Trp Ser Gly Asn Cys Gly Asn Thr Ala His Cys Asp Asn Gln
        35                  40                  45

Cys Arg Ser Trp Glu His Ala Gln His Gly Ala Cys His Val Arg Gly
    50                  55                  60

Gly Lys His Met Cys Phe Cys Tyr Phe Asn Cys
65                  70                  75


<210> SEQ ID NO 38
<211> LENGTH: 23
<212> TYPE: DNA
<213> ORGANISM: Artificial Sequence
<220> FEATURE:
<223> OTHER INFORMATION: PCR primer

<400> SEQUENCE: 38

gctcgagatg gccaacaagc atc                                             23


<210> SEQ ID NO 39
<211> LENGTH: 24
<212> TYPE: DNA
<213> ORGANISM: Artificial Sequence
<220> FEATURE:
<223> OTHER INFORMATION: PCR primer

<400> SEQUENCE: 39

cacatgtgtt tgcctcctct aacg                                            24


<210> SEQ ID NO 40
```

-continued

<211> LENGTH: 24
<212> TYPE: DNA
<213> ORGANISM: Artificial Sequence
<220> FEATURE:
<223> OTHER INFORMATION: PCR primer

<400> SEQUENCE: 40
tccactcgag cggctataaa tacg 24

<210> SEQ ID NO 41
<211> LENGTH: 24
<212> TYPE: DNA
<213> ORGANISM: Artificial Sequence
<220> FEATURE:
<223> OTHER INFORMATION: PCR primer

<400> SEQUENCE: 41
ctttgcgtcc ttgaaaagtc catg 24

<210> SEQ ID NO 42
<211> LENGTH: 24
<212> TYPE: DNA
<213> ORGANISM: Artificial Sequence
<220> FEATURE:
<223> OTHER INFORMATION: PCR primer

<400> SEQUENCE: 42
ggccaatcca gaagatggac aagt 24

<210> SEQ ID NO 43
<211> LENGTH: 22
<212> TYPE: DNA
<213> ORGANISM: Artificial Sequence
<220> FEATURE:
<223> OTHER INFORMATION: PCR primer

<400> SEQUENCE: 43
cgcaagaccg gcaacaggat tc 22

<210> SEQ ID NO 44
<211> LENGTH: 40
<212> TYPE: DNA
<213> ORGANISM: Artificial Sequence
<220> FEATURE:
<223> OTHER INFORMATION: Gene specific primer for RT-PCR amplification

<400> SEQUENCE: 44
cccgggctcg agatggccaa caagcatctt tctctcagtc 40

<210> SEQ ID NO 45
<211> LENGTH: 40
<212> TYPE: DNA
<213> ORGANISM: Artificial Sequence
<220> FEATURE:
<223> OTHER INFORMATION: Gene specific primer for RT-PCR amplification

<400> SEQUENCE: 45
ccatggtacc ttaacagtta aaataacaga agcacatgtg 40

<210> SEQ ID NO 46
<211> LENGTH: 461
<212> TYPE: DNA
<213> ORGANISM: Helianthus annuus
<220> FEATURE:
<221> NAME/KEY: CDS
<222> LOCATION: (14)...(340)

```
<400> SEQUENCE: 46

gcacgagtga aaa atg gcc aaa aat tca gtt gtt ttc tat gca ttt ctt        49
               Met Ala Lys Asn Ser Val Val Phe Tyr Ala Phe Leu
                1               5                   10

ctg ctt ctc ttt gtt ctt gct atc tca gaa atc gga tcg gtg aag gga       97
Leu Leu Leu Phe Val Leu Ala Ile Ser Glu Ile Gly Ser Val Lys Gly
         15                  20                  25

gaa tta tgt gag aag gca agc aag aca tgg tcc gga aaa tgt ggc aac      145
Glu Leu Cys Glu Lys Ala Ser Lys Thr Trp Ser Gly Lys Cys Gly Asn
     30                  35                  40

aca aga cac tgt gac gac cag tgc aag tct tgg gag ggt gca gcc cat      193
Thr Arg His Cys Asp Asp Gln Cys Lys Ser Trp Glu Gly Ala Ala His
 45                  50                  55                  60

gga gct tgt cac gtg cgc ggt ggg aaa cac atg tgc ttc tgc tac ttc      241
Gly Ala Cys His Val Arg Gly Gly Lys His Met Cys Phe Cys Tyr Phe
                 65                  70                  75

aac tgt tcc aaa gcc cag aag ttg gct cag gat aaa ctc ata gca gaa      289
Asn Cys Ser Lys Ala Gln Lys Leu Ala Gln Asp Lys Leu Ile Ala Glu
             80                  85                  90

gag ctc gcc aag gag aag att gaa gcc gaa aag gtg ata gcc aaa cct      337
Glu Leu Ala Lys Glu Lys Ile Glu Ala Glu Lys Val Ile Ala Lys Pro
         95                 100                 105

tga gtagcaaatg ttatatgatt atgaataaag tgaaaatgct agctacttag           390
 *

catataaagc atttcttgt ggtgtaatgt ttgttgcatt tgaaatcagt tgcttcatta    450

tgattccatg c                                                          461


<210> SEQ ID NO 47
<211> LENGTH: 108
<212> TYPE: PRT
<213> ORGANISM: Helianthus annuus

<400> SEQUENCE: 47

Met Ala Lys Asn Ser Val Val Phe Tyr Ala Phe Leu Leu Leu Leu Phe
 1               5                  10                  15

Val Leu Ala Ile Ser Glu Ile Gly Ser Val Lys Gly Glu Leu Cys Glu
            20                  25                  30

Lys Ala Ser Lys Thr Trp Ser Gly Lys Cys Gly Asn Thr Arg His Cys
        35                  40                  45

Asp Asp Gln Cys Lys Ser Trp Glu Gly Ala Ala His Gly Ala Cys His
    50                  55                  60

Val Arg Gly Gly Lys His Met Cys Phe Cys Tyr Phe Asn Cys Ser Lys
65                  70                  75                  80

Ala Gln Lys Leu Ala Gln Asp Lys Leu Ile Ala Glu Glu Leu Ala Lys
                85                  90                  95

Glu Lys Ile Glu Ala Glu Lys Val Ile Ala Lys Pro
            100                 105


<210> SEQ ID NO 48
<211> LENGTH: 529
<212> TYPE: DNA
<213> ORGANISM: Vernonia mespilifolia
<220> FEATURE:
<221> NAME/KEY: misc_feature
<222> LOCATION: 480, 515, 521, 529
<223> OTHER INFORMATION: n = A,T,C or G
<220> FEATURE:
<221> NAME/KEY: CDS
<222> LOCATION: (25)...(372)
```

-continued

```
<400> SEQUENCE: 48

cttgagcttc attctaattc aaaa atg gtg caa aaa tcg att gtt ttc tcc        51
                           Met Val Gln Lys Ser Ile Val Phe Ser
                            1               5

gcg ttc ctt cta atc ctc ttt atc tca gaa atc tcg agt gtg aga gca       99
Ala Phe Leu Leu Ile Leu Phe Ile Ser Glu Ile Ser Ser Val Arg Ala
 10                  15                  20                  25

gag cta tgc gag aaa gct agc aag aca tgg tca ggc aac tgt ggc aac      147
Glu Leu Cys Glu Lys Ala Ser Lys Thr Trp Ser Gly Asn Cys Gly Asn
                 30                  35                  40

aca gga cat tgt gat aat cag tgt aag tca tgg gag ggt gca gcc cat      195
Thr Gly His Cys Asp Asn Gln Cys Lys Ser Trp Glu Gly Ala Ala His
             45                  50                  55

gga gct tgt cat gtg cgt gga ggg aaa cac atg tgc ttt tgt tat ttc      243
Gly Ala Cys His Val Arg Gly Gly Lys His Met Cys Phe Cys Tyr Phe
         60                  65                  70

aat tgt aaa aaa gct gaa aaa ctc gct caa gat aag cta aaa gca gaa      291
Asn Cys Lys Lys Ala Glu Lys Leu Ala Gln Asp Lys Leu Lys Ala Glu
     75                  80                  85

gag ctt gct aaa gac aaa ctc aag gca gat aag ttt gac cat gat gca      339
Glu Leu Ala Lys Asp Lys Leu Lys Ala Asp Lys Phe Asp His Asp Ala
 90                  95                 100                 105

aaa gaa gta gta cca aat gtc gaa cat cca tga aagatcggtt tccttaaatc    392
Lys Glu Val Val Pro Asn Val Glu His Pro  *
                110                 115

aatagctgtt ttaataagtt atgaataaaa acagaaagtg ttgtataatc atatttttag    452

cttccttaga gatgcattat gttgcaantc cacaacttct tgtggtaaat gtgtaaaatg    512

tangatacna aagctan                                                   529


<210> SEQ ID NO 49
<211> LENGTH: 115
<212> TYPE: PRT
<213> ORGANISM: Vernonia mespilifolia

<400> SEQUENCE: 49

Met Val Gln Lys Ser Ile Val Phe Ser Ala Phe Leu Leu Ile Leu Phe
 1               5                  10                  15

Ile Ser Glu Ile Ser Ser Val Arg Ala Glu Leu Cys Glu Lys Ala Ser
            20                  25                  30

Lys Thr Trp Ser Gly Asn Cys Gly Asn Thr Gly His Cys Asp Asn Gln
        35                  40                  45

Cys Lys Ser Trp Glu Gly Ala Ala His Gly Ala Cys His Val Arg Gly
    50                  55                  60

Gly Lys His Met Cys Phe Cys Tyr Phe Asn Cys Lys Lys Ala Glu Lys
65                  70                  75                  80

Leu Ala Gln Asp Lys Leu Lys Ala Glu Glu Leu Ala Lys Asp Lys Leu
                85                  90                  95

Lys Ala Asp Lys Phe Asp His Asp Ala Lys Glu Val Val Pro Asn Val
            100                 105                 110

Glu His Pro
        115


<210> SEQ ID NO 50
<211> LENGTH: 24
<212> TYPE: PRT
<213> ORGANISM: Hordeum vulgare

<400> SEQUENCE: 50
```

-continued

```
Met Ala Asn Lys His Leu Ser Leu Ser Leu Phe Leu Val Leu Leu Gly
 1               5                  10                  15

Leu Ser Ala Ser Leu Ala Ser Gly
            20


<210> SEQ ID NO 51
<211> LENGTH: 40
<212> TYPE: PRT
<213> ORGANISM: Artificial Sequence
<220> FEATURE:
<223> OTHER INFORMATION: Consensus sequence generated by the amino acid
      alignment of selected protein sequences of the
      invention.

<400> SEQUENCE: 51

Leu Cys Glu Ala Ser Thr Trp Ser Gly Cys Gly Asn Thr His Cys Asp
 1               5                  10                  15

Gln Cys Ser Trp Glu Ala His Gly Ala Cys His Val Arg Gly Lys His
            20                  25                  30

Met Cys Phe Cys Tyr Phe Asn Cys
        35                  40
```

NUCLEIC ACIDS ENCODING PLANT DEFENSINS AND METHODS OF USE THEREOF

CROSS-REFERENCE TO RELATED APPLICATIONS

This is a continuation-in-part of U.S. application Ser. No. 10/030,516 filed Oct. 25, 2001, now abandoned, which is a 371 of PCT Application PCT/US00/11952, filed May 3, 2000, which claims the benefit of U.S. Provisional Application No. 60/133,039, filed May 7, 1999, the contents of which are hereby incorporated by reference in their entirety.

FIELD OF THE INVENTION

This invention is in the field of plant molecular biology. More specifically, this invention pertains to nucleic acid molecules that encode plant defensins.

BACKGROUND OF THE INVENTION

Defensins are small, basic, cysteine-rich proteins that exhibit broad antipathogenic activity through the formation of multimeric pores in outer or inner biological membranes. The multimeric pores lead to membrane disruption and depolarization. Defensins have a wide phylogenetic distribution, having been found in insects, mammals, and plants.

Although plant defensins have only been identified recently and are not as well characterized as their mammalian and insect counterparts, several lines of observation suggest the importance of defensins in mediating host resistance to pathogen attack. Plant defensins have been shown to induce a rapid K+ efflux and $Ca_2$+ influx in fungal hyphae as well as alkalinization of the incubation medium. The operating mechanism however appears not to involve direct defensin-membrane interactions, but rather a different, possibly receptor-mediated, event (Thevissen, K., et al. (1996) *J. Biol. Chem.* 271:15018–15025). Defensins have also been shown to accumulate systemically upon challenge by fungal pathogens (Manners, J. M., et al. (1998) *Plant Mol. Biol.* 38:1071–1080; Terras, F. R., et al. (1998) *Planta* 206:117–124; Terras, F. R., et al. (1995) *Plant Cell* 7:573–588). Furthermore, transgenic tobacco that constitutively expressed a radish defensin was found to have improved resistance to infection by a fungal pathogen (Terras, F. R et al., (1995) Plant Cell 7:573–588).

Defensins have been shown to be induced by artificial drought (Maitra, N. and Cushman, J. C. (1998) *Plant Physiol.* 118:1536) and salt stress (Yamada, S., et al. (1997) *Plant Physiol.* 115:314) suggesting that these proteins may play a more general role in stress tolerance, one that is not restricted to pathogen attack.

Defensin molecules may be used in transgenic plants in order to produce plants with increased resistance to pathogens such as fungi, viruses, bacteria, nematodes, and insects. Thus, the present invention solves needs for the enhancement of a plant's defensive response via a molecularly based mechanism that can be quickly incorporated into commercial crops.

SUMMARY OF THE INVENTION

Compositions and methods relating to pathogen resistance are provided.

The defensin sequences of the present invention find use in enhancing the plant pathogen defense system. The compositions and methods of the invention can be used for enhancing resistance to plant pathogens including fungal pathogens, plant viruses, microorganisms, nematodes, insects, and the like. The method involves stably transforming a plant with a nucleotide sequence capable of modulating the plant pathogen defense system operably linked with a promoter capable of driving expression of a gene in a plant cell. The defensin sequences additionally find use in manipulating these processes in transformed plants and plant cells.

Transformed plants, plant cells, and seeds, as well as methods for making such plants, plant cells, and seeds, are additionally provided. It is recognized that a variety of promoters will be useful in the invention, the choice of which will depend in part upon the desired level of expression of the disclosed defensin sequences. It is recognized that the levels of expression can be controlled to modulate the levels of expression in the plant cell.

The present invention concerns isolated polynucleotides comprising a nucleotide sequence selected from the group consisting of: a nucleotide sequence set forth in SEQ ID NO: 1, 3, 5, 7, 9, 11, 13, 15, 17, 19, 21, 23, 25, 27, 29, 31, 46, or 48; a nucleotide sequence that encodes a polypeptide having the amino acid sequence set forth in SEQ ID NO: 2, 4, 6, 8, 10, 12, 14, 16, 18, 20, 22, 24, 26, 28, 32, 47, or 49; a nucleotide sequence that encodes a mature polypeptide having the amino acid sequence set forth in SEQ ID NO: 35; a nucleotide sequence characterized by at least 75% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 80% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 85% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 90% sequence identity to the nucleotide sequence set forth in SEQ ID NO: 1, 3, 5, 7, 9, 11, 13, 15, 17, 19, 21, 23, 25, 27, 29, 31, 46, or 48; and a nucleotide sequence that comprises the complement of any one of the above.

In a further embodiment the isolated polynucleotide of the claimed invention comprises a nucleotide sequence selected from the group consisting of SEQ ID NOs: 1, 3, 5, 7, 9, 11, 13, 15, 17, 19, 21, 23, 25, 27, 29, 31, 46, or 48, that codes for the polypeptide selected from the group consisting of SEQ ID NOs: 2, 4, 6, 8, 10, 12, 14, 16, 18, 20, 22, 24, 26, 28, 30, 32, 47, or 49.

This invention also relates to a chimeric gene comprising an isolated polynucleotide of the present invention operably linked to suitable regulatory sequences.

In yet a further embodiment, the present invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention further provides a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention also provides an isolated polypeptide selected from the group consisting of: a polypeptide comprising an amino acid sequence set forth in SEQ ID NO: 2, 4, 6, 8, 10, 12, 14, 16, 18, 20, 22, 24, 26, 28, 32, 47, or 49; a polypeptide characterized by at least 80% identity to SEQ ID NO: 6, 26, or 28; a polypeptide characterized by at least 85% identity to SEQ ID NO: 8; a polypeptide characterized by at least 95% identity to SEQ ID NO: 2, 4, 10, 12, 14, 16, 18, 20, 22, 24, or 47; a polypeptide characterized by at least 97% identity to SEQ ID NO: 32; and the polypeptide of SEQ ID NO: 49.

In a further embodiment, the invention relates to a method of selecting an isolated polynucleotide that affects the level of expression of a plant defensin polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the plant defensin polypeptide or enzyme activity in the host cell containing the isolated polynucleotide; and (d) comparing the level of the plant defensin polypeptide or enzyme activity in the host cell containing the isolated polynucleotide with the level of the plant defensin polypeptide or enzyme activity in the host cell that does not contain the isolated polynucleotide.

A method for impacting a plant pathogen comprising introducing into a plant or cell thereof at least one nucleotide construct comprising a nucleotide sequence operably linked to a promoter that drives expression of a gene in plant cells, wherein said nucleotide sequence is selected from the group consisting of: a nucleotide sequence set forth in SEQ ID NO: 1, 3, 5, 7, 9, 11, 13, 15, 17, 19, 21, 23, 25, 27, 29, 31, 46, or 48; a nucleotide sequence that encodes a polypeptide having the amino acid sequence set forth in SEQ ID NO: 2, 4, 6, 8, 10, 12, 14, 16, 18, 20, 22, 24, 26, 28, 32, 47, or 49; a nucleotide sequence that encodes a mature polypeptide having the amino acid sequence set forth in SEQ ID NO: 35; a nucleotide sequence characterized by at least 75% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 80% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 85% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 90% sequence identity to the nucleotide sequence set forth in SEQ ID NO: 1, 3, 5, 7, 9, 11, 13, 15, 17, 19, 21, 23, 25, 27, 29, 31, 46, or 48; and a nucleotide sequence that comprises the complement of any one of the above is also provided.

Expression cassettes and stably transformed plants comprising one or more of the defensin sequences of the invention are also provided. The polypeptides of the present invention are useful in protecting plants from various pests including, but not limited to, insects, fungi, and nematodes.

The invention provides nucleic acid molecules comprising nucleotide sequences, and fragments and variants thereof, that encode polypeptides or mature polypeptides that possess activity against plant pathogens. In some embodiments, the nucleotide sequences encode polypeptides that are pesticidal against nematodes. In other embodiments, the nucleotide sequences encode polypeptides that are active against fungal pathogens.

In a particular embodiment, a transformed plant of the invention can be produced using a defensin nucleotide sequence of the invention that has been optimized for increased expression in a host plant. For example, the defensin-like polypeptides of the invention can be back-translated to produce nucleic acids comprising codons optimized for expression in a particular host, for example a crop plant such as a soybean plant. In some embodiments, the invention provides transgenic plants expressing polypeptides that find use in methods for impacting various plant pathogens.

BRIEF DESCRIPTION OF THE DRAWING AND SEQUENCE DESCRIPTIONS

The invention can be more fully understood from the following detailed description and the accompanying drawings and Sequence Listing that form a part of this application.

FIG. 1 depicts the amino acid sequence alignment between the defensin encoded by the nucleotide sequences derived from *Dimorphotheca sinuata* clone dms2c.pk001.d3 (SEQ ID NO: 4); *Picramnia pentandra* clone pps.pk0011.a9 (SEQ ID NO: 8); *Parthenium argentatum* Grey clones epb1c.pk002.h2 (SEQ ID NO: 12), epb1c.pk001.h15 (SEQ ID NO: 14), epb1c.pk003.p14 (SEQ ID NO: 16), epb1c.pk004.p22 (SEQ ID NO: 18), epb1c.pk005.o6 (SEQ ID NO: 20), epb1c.pk006.k15 (SEQ ID NO: 22), and epb3c.pk009.j22 (SEQ ID NO: 24); and *Nicotiana benthamiana* clone tdr1c.pk002.g7 (SEQ ID NO:28); and the defensin polypeptide isolated from *Dahlia merckii* (NCBI GenBank Identifier (GI) No. 2147320; SEQ ID NO:33). Amino acids that are conserved among all and at least two sequences with an amino acid at that position are indicated with an asterisk (*). Dashes are used by the program to maximize alignment of the sequences.

FIG. 2 depicts the amino acid sequence alignment between the defensin encoded by the nucleotide sequences derived from *Picramnia pentandra* clone pps.pk0010.g2, also referred to as Pps-AMP1, (SEQ ID NO: 30); *Vernonia mespilifolia* clone vs1n.pk0009.h6 (SEQ ID NO: 32); *Helianthus annuus* clone hss1c.pk018.k14 (SEQ ID NO: 47); *Vernonia mespilifolia* clone vs1n.pk007.a9 (SEQ ID NO: 49); and the defensin polypeptide isolated from *Dahlia merckii* (NCBI GenBank Identifier (GI) No. 2147320; SEQ ID NO: 33). Amino acids that are conserved among each of the sequences shown are identified in the consensus sequence (represented as SEQ ID NO: 51 in the sequence listing). Dots are used by the program to maximize alignment of the sequences. The alignment shown in FIG. 2 was generated by the PILEUP program available in the Wisconsin Genetics Software Package (available from Genetics Computer Group (GCG), 575 Science Drive, Madison, Wis. USA).

FIG. 3 depicts the results obtained from Soybean Cyst Nematode (SCN; *Heterodera glycines*) assays on soybean plants transformed with a vector comprising the UCP1 promoter, the Barley Alpha Amylase (BAA) signal sequence, and the mature peptide region of the clone designated pps.pk0010.g2, also known as Pps-AMP1. Average number of cysts for the Jack soybean cultivar representing T0 transformants that did not contain the heterologous DNA (Neg control); the Essex soybean variety 9 which is susceptible to SCN); and selected PCR positive T0 UCP1:BAA-mature PpsAMP1 transformants. Measurements are based on 3 plants/event.

Figure 4:
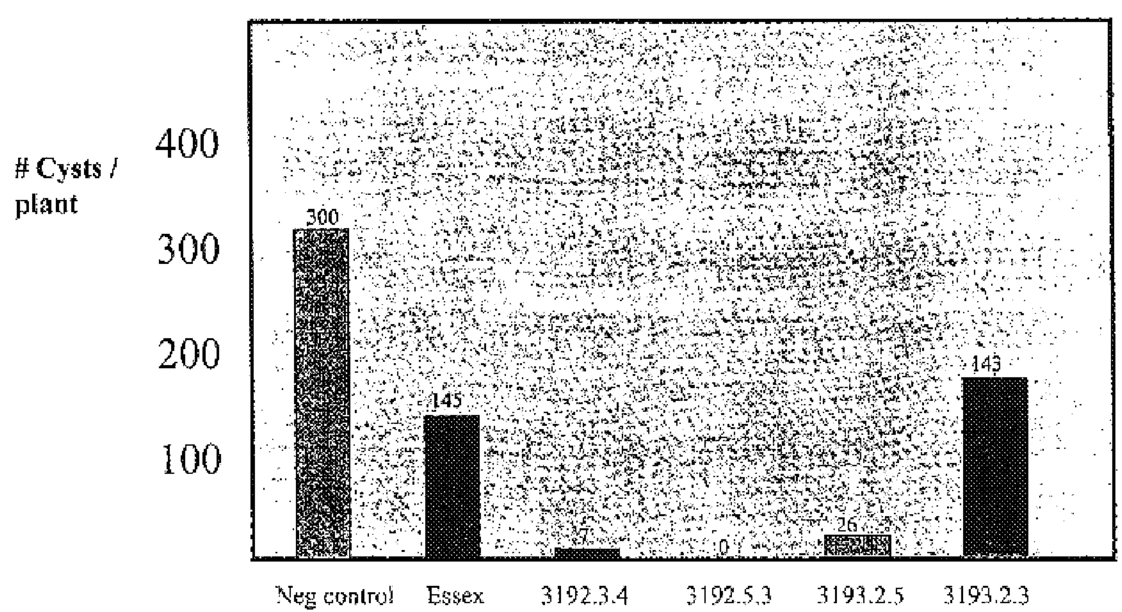

FIG. 4 depicts the results obtained from SCN assays on soybean plants transformed with a vector comprising the IFS1 promoter, the BAA signal sequence, and the mature peptide region of Pps-AMP1. Average number of cysts for the Jack soybean cultivar representing T0 transformants that did not contain the heterologous DNA (Neg control); the Essex soybean variety (which is susceptible to SCN); and selected PCR positive T0 IFS1:BAA-mature PpsAMP1 transformants. Measurements are based on 3 plants/event.

Figure 5:
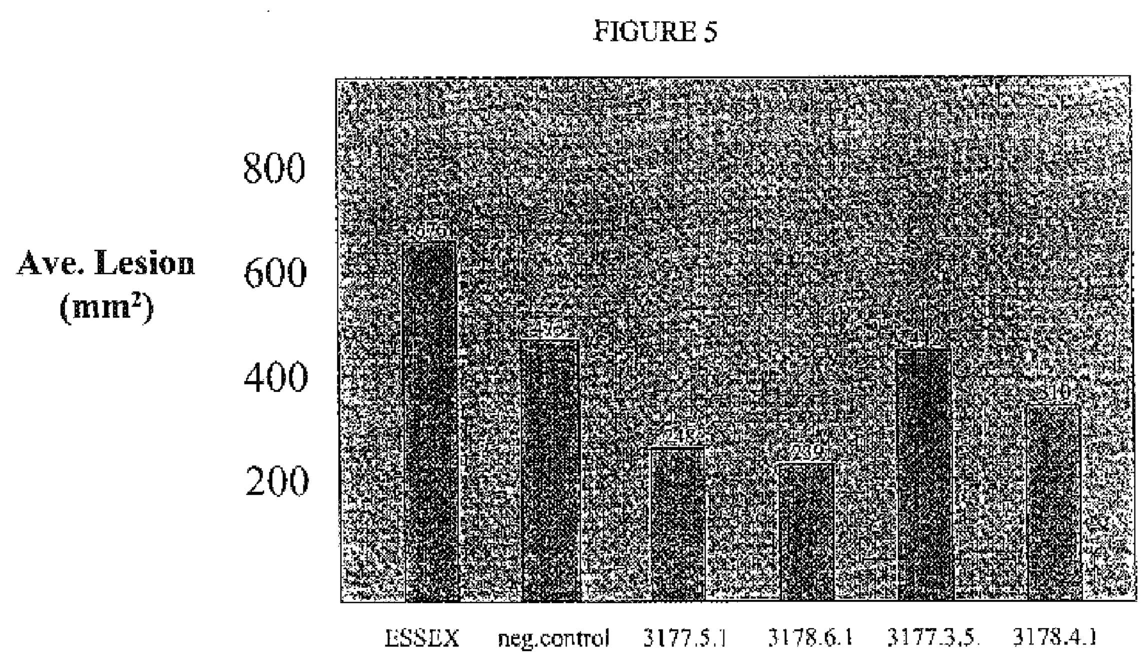

FIG. 5 depicts the results obtained from *Sclerotinia sclerotiorum* leaf assays on soybean plants transformed with a vector comprising the UCP1 promoter, the BAA signal sequence and the mature peptide region of Pps-AMP1. Average lesion size for Essex soybean leaves (a variety susceptible to SCN); Jack soybean cultivar leaves representing T0 transformants that did not contain the heterologous DNA (Neg control); and selected transgenic UCP1:BAA-mature Pps-AMP1 T0 plants. Measurements are based on 3 plants/event, 2 leaves/plant. Two measurements were made across the widest tranects of the lesion and then multiplied to give an approximate surfact area for thelesion.

Figure 6:
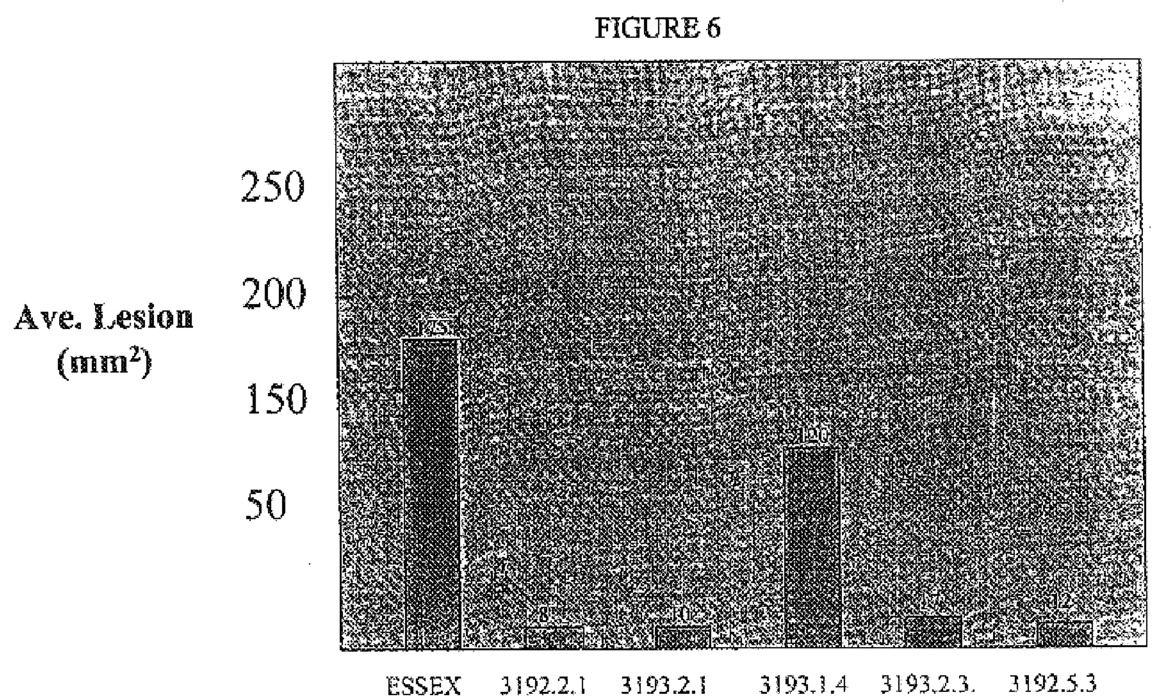

FIG. 6 depicts the results obtained from *Sclerotinia sclerotiorum* leaf assays on soybean plants transformed with a vector comprising the IFS1 promoter, the BAA signal sequence, and the mature peptide region of Pps-AMP1. Average lesion size for control Essex soybean leaves and selected transgenic IFS1:BAA-mature PpsAMP1 T0 plants. Measurements are based on 3 plants/event, 2 leaves/plant. Two measurements were made across the widest transects of the lesion and then multiplied to give an approximate surface area for the lesion.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding at a minimum the mature protein derived from an EST, FIS, a contig, or an FIS and PCR ("CGS"). Nucleotide SEQ ID NOs: 1, 5, 9, and 25 correspond to nucleotide SEQ ID NOs: 1, 5, 3, and 7, respectively, presented in U.S. Provisional Application No. 60/133,039, filed May 7, 1999. Amino acid SEQ ID NOs: 2, 6, 10, and 26 correspond to amino acid SEQ ID NOs: 2, 6, 4, and 8, respectively, presented in U.S. Provisional Application No. 60/133,039, filed May 7, 1999. The sequence descriptions and Sequence Listing attached hereto comply with the rules governing nucleotide and/or amino acid sequence disclosures in patent applications as set forth in 37 C.F.R. §1.821–1.825.

TABLE 1

Plant Defensins

| Protein (Plant Source) | Clone Designation | Status | SEQ ID NO: (Nucleotide) | SEQ ID NO: (Amino Acid) |
|---|---|---|---|---|
| Plant Defensin (*Dimorphotheca sinuata*) | dms2c.pk001.d3 | EST | 1 | 2 |
| Plant Defensin (*Dimorphotheca sinuata*) | dms2c.pk001.d3(FIS) | CGS | 3 | 4 |
| Plant Defensin (*Picramnia pentandra*) | pps.pk0011.a9 | EST | 5 | 6 |
| Plant Defensin (*Picramnia pentandra*) | pps.pk0011.a9(FIS) | CGS | 7 | 8 |
| Plant Defensin (*Parthenium argentatum* Grey) | epb1c.pk002.h2(EST) | CGS | 9 | 10 |
| Plant Defensin (*Parthenium argentatum* Grey) | epb1c.pk002.h2(FIS) | CGS | 11 | 12 |
| Plant Defensin (*Parthenium argentatum* Grey) | epb1c.pk001.h15(EST) | CGS | 13 | 14 |
| Plant Defensin (*Parthenium argentatum* Grey) | epb1c.pk003.p14(EST) | CGS | 15 | 16 |
| Plant Defensin (*Parthenium argentatum* Grey) | epb1c.pk004.p22(EST) | CGS | 17 | 18 |
| Plant Defensin (*Parthenium argentatum* Grey) | epb1c.pk005.o6(EST) | CGS | 19 | 20 |
| Plant Defensin (*Parthenium argentatum* Grey) | epb1c.pk006.k15(EST) | CGS | 21 | 22 |
| Plant Defensin (*Parthenium argentatum* Grey) | epb3c.pk009.j22(EST) | CGS | 23 | 24 |
| Plant Defensin (*Nicotiana benthamiana*) | tdr1c.pk002.g7(EST) | CGS | 25 | 26 |
| Plant Defensin (*Nicotiana benthamiana*) | tdr1c.pk002.g7(FIS) | CGS | 27 | 28 |
| Plant Defensin (*Picramnia pentandra*) | pps.pk0010.g2 (FIS) | CGS | 29 | 30 |
| Plant Defensin (*Vernonia mespilifolia*) | vs1n.pk0009.h6 (FIS) | CGS | 31 | 32 |
| Plant Defensin (*Helianthus annuus*) | hss1c.pk018.k14(FIS) | CGS | 46 | 47 |
| Plant Defensin (*Vernonia mespilifolia*) | vs1n.pk007.a9(FIS) | CGS | 48 | 49 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No.

2):345–373 (1984), which are herein incorporated by reference. The symbols and format used for nucleotide and amino acid sequence data comply with the rules set forth in 37 C.F.R. §1.822.

DETAILED DESCRIPTION OF THE INVENTION

The present invention provides, inter alia, compositions and methods for modulating the total level of polypeptides of the present invention and/or altering their ratios in a plant. By "modulation" an increase or decrease in a particular character, quality, substance, or response is intended. The compositions comprise nucleotide and amino acid sequence from various plant species.

By "plant defensin genes", is intended genes that are structurally related to plant defensins, and include thionins, small cysteine-rich peptides, proteinase inhibitors, amylase inhibitors, and the like. They are called defensin genes after a structural classification of proteins (SCOP) classification system. Defensins play a role in defense, more specifically plant defense against pathogens, and they share similarity in primary and secondary structure with insect defensins. While not bound by any mechanism of action, expression of the sequences and related genes around disease-induced lesions may control symptom development, as in a hypersensitive response (HR), by controlling the protease-mediated cell death mechanism. The compositions may also function directly as antipathogenic proteins by inhibiting proteases produced by pathogens or by binding cell wall components of pathogens. Thirdly, they may also act as amphipathic proteins that perturb membrane function, leading to cellular toxicity of the pathogens. These small cysteine-rich peptides demonstrate antimicrobial activity. By "antimicrobial" or "antimicrobial activity" is intended antibacterial, antiviral, antinematocidal, insecticidal, and antifungal activity. Accordingly, the polypeptides of the invention may enhance resistance to insects and nematodes. Any one defensin exhibits a spectrum of antimicrobial activity that may involve one or more antibacterial, antifungal, antiviral, insecticidal, antinematocidal, or antipathogenic activities. They may also be useful in regulating seed storage protein turnover and metabolism.

Plant defensins generally comprise about 45–54 amino acids with four disulfide bridges (Broekaert et al. (1995) *Plant Physiol.* (Bethesda) 108:1353–1358). The defensin genes of the present invention find use in enhancing the plant pathogen defense system. The defensins of the invention inhibit the growth of a broad range of pathogens, including but not limited to fungi, bacteria, nematodes, insects, and viruses, at micromolar concentrations. Thus, by "defensin-like activity" it is intended that the peptides inhibit pathogen growth or damage caused by a variety of pathogens, including, but not limited to, fungi, insects, nematodes, viruses, and bacteria. Defensins inhibit pathogen damage through a variety of mechanisms including, but not limited to, alteration of membrane ion permeability and induction of hyphal branching in fungal targets (Garcia-Olmeda et al. (1998) *Biopolymers, Peptide Science* 47:479–491, herein incorporated by reference).

The compositions of the invention can be used in a variety of methods whereby the protein products can be expressed in crop plants to function as antimicrobial proteins. The compositions of the invention may be expressed in a crop plant such as the soybean to function as an antifungal agent, an antinematocidal agent, and the like. Expression of the proteins of the invention will result in alterations or modulation of the level, tissue, or timing of expression to achieve enhanced disease, insect, nematode, viral, fungal, or stress resistance. The compositions of the invention may be expressed in the native species including, but not limited to *Dimorphotheca sinuata, Picramnia pentandra, Parthenium argentatum* Grey, *Nicotiana benthamiana, Vernonia mespilifolia*, and *Helianthus annuus*, or alternatively, can be heterologously expressed in any plant of interest. In this manner, the coding sequence for the defensin can be used in combination with a promoter that is introduced into a crop plant. In one embodiment, a high-level expressing constitutive promoter may be utilized and would result in high levels of expression of the defensin. In other embodiments, the coding sequence may be operably linked to a tissue-preferred promoter to direct the expression to a plant tissue known to be susceptible to a pathogen. Likewise, manipulation of the timing of expression may be utilized. For example, by judicious choice of promoter, expression can be enhanced early in plant growth to prime the plant to be responsive to pathogen attack. Likewise, pathogen inducible promoters can be used wherein expression of the defensin is turned on in the presence of the pathogen.

If desired, a transit peptide can be utilized to direct cellular localization of the protein product. In this manner, the native transit peptide or a heterologous transit peptide can be used. However, it is recognized that both extracellular expression and intracellular expression are encompassed by the methods of the invention.

Sequences of the invention, as discussed in more detail below, encompass coding sequences, antisense sequences, and fragments and variants thereof. Expression of the sequences of the invention can be used to modulate or regulate the expression of corresponding defensin proteins.

The compositions and methods of the invention can be used for enhancing resistance to plant pathogens including fungal pathogens, plant viruses, insect pathogens, bacterial pathogens, nematodes, and the like. The method involves stably transforming a plant with a nucleotide sequence capable of modulating the plant pathogen defense system operably linked with a promoter capable of driving expression of a gene in a plant cell. By "enhancing resistance" increasing the tolerance of the plant to pathogens is intended. That is, the defensin may slow or prevent pathogen infection and/or spread.

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs: 1, 3, 5, 7, 9, 11, 13, 15, 17, 19, 21, 23, 25, 27, 29, 31, 46, or 48, or the complement of such sequences.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment.

Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through, for example, antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment that result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 46, or 48, and the complement of such nucleotide sequences may be used in methods of selecting an isolated polynucleotide that affects the expression of a plant defensin polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) *Nucleic Acid Hybridisation*, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Specificity is typically the function of post-hybridization washes, the critical factors being the ionic strength and temperature of the final wash solution. For DNA-DNA hybrids, the Tm can be approximated from the equation of Meinkoth and Wahl (1984) *Anal. Biochem.* 138:267–284: Tm=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with>90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC, 0.1% SDS at 65° C.

Thus, isolated sequences that encode a defensin polypeptide and which hybridize under stringent conditions to the defensin sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

The GAP program uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can each be 0, 1, 2, 3, 4, 5, 6, 7, 8, 9, 10, 15, 20, 25, 30, 35, 40, 45, 50, 55, 60, 65 or greater. The scoring matrix used in Version 10 of the Wisconsin Genetics Software Package is BLOSUM62 (see Henikoff and Henikoff (1989) *Proc. Natl. Acad. Sci. USA* 89:10915).

The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences.

The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTN program, score=50, wordlength=3, to obtain amino acid sequences homologous to a protein or polypeptide of the invention. To obtain gapped alignments for comparison purposes. Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g. BLASTN for nucleotide sequences, BLASTX for proteins) can be used. Alignment may also be performed manually by inspection.

Unless otherwise indicated, sequence alignments and percent identity calculations were performed using the Megalign program of the LASERGENE bioinformatics computing suite (DNASTAR Inc., Madison, Wis.), or any equivalent program. Multiple alignment of the sequences was performed using the Clustal method of alignment (Higgins and Sharp (1989) *CABIOS* 5:151–153) with the default parameters (GAP PENALTY=10, GAP LENGTH PENALTY=10), while default parameters for pairwise alignments using the Clustal method were KTUPLE 1, GAP PENALTY=3, WINDOW=5 and DIAGONALS SAVED=5, unless otherwise indicated.

By "equivalent program" any sequence comparison program that, for any two sequences in question, generates an alignment having identical nucleotide or amino acid residue matches and an identical percent sequence identity when compared to the corresponding alignment generated by the preferred program is intended.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule., When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e, gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

As used herein, "fill-length sequence" in reference to a specified polynucleotide or its encoded protein means having the entire nucleic acid sequence or the entire amino acid sequence of a native (non-synthetic), endogenous sequence. A full-length polynucleotide encodes the full-length, catalytically active form of the specified protein.

The term "substantial identity" of polynucleotide sequences means that a polynucleotide comprises a sequence that has at least 70% sequence identity, preferably at least 75%, 80%, 85%, 86%, 87%, 88%, 89%, 90%, 91%, 92%, 93%, 94%, 95%, 96%, 97%, 98%, or 99% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 75%, 80%, 85%, 90%, 91%, 92%, 93%, 94%, 95%, 96%, 97%, 98%, and 99%.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The term "substantial identity" in the context of a peptide indicates that a peptide comprises a sequence with at least 70% sequence identity to a reference sequence, preferably 80%, more preferably 85%, most preferably at least 90%, 91%, 92%, 93%, 94%, 95%, 96%, 97%, 98%, or 99% sequence identity to the reference sequence over a specified comparison window. Preferably, optimal alignment is conducted using the homology alignment algorithm of Needleman et al. (1970) J. Mol. Biol. 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence often or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., to situ hybridization of bacterial colonies or bacteriophage plaque.). In addition, short oligonucleatides of 12 or more nucleotides may be use as amplification primers in PCR in order to obtain a particular nucleic acid fragment comprising the primtrs. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have defensin-like activity and thereby affect development, developmental pathways, and defense responses. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a defensin nucleotide sequence that encodes a biologically active portion of a defensin protein of the invention will encode at least 15, 25, 30, 50, 100, 150, 153, 200, 250, 300, contiguous amino acids, or up to the total number of amino acids present in a full-length protein of the invention. Fragments of a defensin nucleotide sequence that are useful as hybridization probes for PCR primers generally need not encode a biologically active portion of a defensin protein.

Thus, a fragment of a defensin nucleotide sequence may encode a biologically active portion of a defensin protein, or it may be a fragment that can be used as a hybridization probe or PCR primer using methods disclosed below. A biologically active portion of a defensin protein can be prepared by isolating a portion of one of the defensin nucleotide sequences of the invention, expressing the encoded portion of the defensin protein (e.g., by recombinant expression in vitro), and assessing the activity of the encoded portion of the defensin protein. Nucleic acid molecules that are fragments of a defensin nucleotide sequence comprise at least 16, 20, 50, 75, 100, 150, 200, 250, 300, 350, 400, 450, 500, 550, 600, 650, 683, 700, 800, or 900 nucleotides, or up to the number of nucleotides present in a full-length defensin nucleotide sequence disclosed herein.

Biological activity of the defensin polypeptides (i.e., influencing the plant defense response and various developmental pathways, including, for example, influencing cell division) can be assayed by any method known in the art (see for example, U.S. Pat. No. 5,614,395; Thomma et al. (1998) *Plant Biology* 95:15107–15111; Liu et al. (1994) *Plant Biology* 91:1888–1892; Hu et al. (1997) *Plant Mol. Biol.* 34:949–959; Cammue et al. (1992) *J. Biol. Chem.* 267:2228–2233; and Thevissen et al. (1996) *J. Biol. Chem.* 271:15018–15025, all of which are herein incorporated by reference). Furthermore, assays to detect defensin-like activity include, for example, assessing antifungal and/or antimicrobial activity (Terras et al. (1992) *J. Biol. Chem.* 267:14301–15309; Terras et al. (1993) *Plant Physiol* (Bethesda) 103:1311–1319; Terras et al. (1995) *Plant Cell* 7:573–588, Moreno et al. (1994) *Eur. J. Biochem.* 223:135–139; and Osborn et al. (1995) *FEBS Lett.* 368:257–262, all of which are herein incorporated by reference).

By "variants" substantially similar sequences are intended. For nucleotide sequences, conservative variants include those sequences that, because of the degeneracy of the genetic code, encode the amino acid sequence of one of the defensin polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a defensin protein of the invention. Generally, variants of a particular nucleotide sequence of the invention will have at least about 50%, 60%, 65%, 70%, generally at least about 75%, 80%, 81%, 82%, 83%, 84%, 85%, 86%, 87%, 88%, 89%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they continue to possess the desired biological activity of the native protein, that is, defensin-like activity as described herein. Such variants may result from, for example, genetic polymorphism or from human manipulation. Biologically active variants of a native defensin protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. For example, amino acid sequence variants of the defensin proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (Macmillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired developmental activity, or defense response activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by defensin activity assays. See, for example, Lancaster et al. (1994) *J. Biol. Chem.* 14:1137–1142 and Terras et al. (1995) *Plant Cell* 7:537–588, herein incorporated by reference. Additionally, differences in the expression of specific genes between uninfected and infected plants can be determined using gene expression profiling. RNA was analyzed using the gene expression profiling process (GeneCalling®) as described in U.S. Pat. No. 5,871,697, herein incorporated by reference.

Variant nucleotide sequences and proteins also encompass sequences and proteins derived from a mutagenic and recombinogenic procedure such as DNA shuffling. With such a procedure, one or more different defensin coding sequences can be manipulated to create a new defensin protein possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell. Determination of preferred codons can be based on a survey of genes derived from the host cell where sequence information is available. For example, the codon frequency tables available on the World Wide Web at Kazusa.orjp/codon/ may be used to determine preferred codons for a variety of organisms. See also Campbell and Gowri (1990) *Plant Physiol.* 92: 1–11; Murray et al. (1989) *Nucleic Acids Res.* 17:477–498, and U.S. Pat. Nos. 5,380,831 and 5,436,391; herein incorporated by reference.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

"Coding sequence" refers to a nucleotide sequence that codes for a specific amino acid sequence. As used herein, the terms "encoding" or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3"non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Underexpression" refers to the production of a gene product in transgenic organisms at levels below that of levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell that either lacks the expression of a certain polypeptide or expresses a polypeptide which is inactive or does not have any detectable expected enzymatic function.

"Mature" protein refers to a post-translationally processed polypeptide; i.e., one from which any pre- or propeptides present in the primary translation product has been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence that is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence that is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal can further be added, or if to the endoplasmic reticulum, an endoplasmic reticulum retention signal may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., (1985; Supp. 1987) *Cloning Vectors: A Laboratory Manual*, Weissbach and Weissbach (1989) *Methods for Plant Molecular Biology*, (Academic Press, New York); and Flevin et al., (1990) *Plant Molecular Biology Manual*, (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. (1989) *Molecular Cloning: A Laboratory Manual*; (2d ed.; Cold Spring Harbor Laboratory Press) Plainview, N.Y., hereinafter referred to as "Maniatis".

"PCR" or "polymerase chain reaction" is a technique used for the amplification of specific DNA segments (U.S. Pat. Nos. 4,683,195 and 4,800,159).

The present invention concerns an isolated polynucleotide comprising a nucleotide sequence selected from the group consisting of: a nucleotide sequence set forth in SEQ ID NO:1, 3, 5, 7, 9, 11, 13, 15, 17, 19, 21, 23, 25, 27, 29, 31, 46, or 48; a nucleotide sequence that encodes a polypeptide having the amino acid sequence set forth in SEQ ID NO: 2, 4, 6, 8, 10, 12, 14, 16, 18, 20, 22, 24, 26, 28, 32, 47, or 49; a nucleotide sequence that encodes a mature polypeptide having the amino acid sequence set forth in SEQ ID NO: 35; a nucleotide sequence characterized by at least 75% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 80% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 85% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 90% sequence identity to the nucleotide sequence set forth in SEQ ID NO: 1, 3, 5, 7, 9, 11, 13, 15, 17, 19, 21, 23, 25, 27, 29, 31, 46, or 48; and a nucleotide sequence that comprises the complement of any one of the above.

Nucleic acid fragments encoding at least a portion of several plant defensins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other plant defensins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis).

Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 46, or 48, and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a defensin polypeptide comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the or consisting of SEQ ID NOS:1, 3, 5, 7, 9, 11, 13, 15, 17, 19, 21, 23, 25, 27, 29, 31, 46, or 48, and the complement of such nucleotide sequences; and amplifying a nucleic acid fragment (preferably a cDNA inserted in a cloning vector) using the oligonucleotide primer. The amplified nucleic acid fragment preferably will encode a portion of a plant defensin polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells that can be used to practice the invention include, but are not limited to, yeast, bacteria, fungus, insect, mammalian, and plant cells.

By "host cell" a cell, which comprises a heterologous nucleic acid sequence of the invention is meant. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' noncoding sequences encoding transcription termination signals may also be provided. The instant chimeric gene may also comprise one or more introns in order to facilitate gene expression.

The defensin sequences of the invention are provided in expression cassettes or DNA constructs for expression in the plant of interest. The cassette will include 5' and 3' regulatory sequences operably linked to a defensin sequence of the invention. The cassette may additionally contain at least one additional gene to be cotransformed into the organism. Alternatively, the additional gene(s) can be provided on multiple expression cassettes.

Such an expression cassette is provided with a plurality of restriction sites for insertion of the defensin sequence to be under the transcriptional regulation of the regulatory regions. The expression cassette may additionally contain selectable marker genes.

The expression cassette will include in the 5'-3' direction of transcription, a transcriptional and translational initiation region, a defensin DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of defensin in the host cell (i.e., plant or plant cell). Thus, the phenotype of the host cell (i.e., plant or plant cell) is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase (NOS) termination regions. See also Guerineau et al. (1991) *Mol. Gen. Genet.* 262:141–144; Proudfoot (1991) *Cell* 64:671–674; Sanfaconetal. (1991) *Genes Dev.* 5:141–149; Mogenetal. (1990) *Plant*

*Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); polyvirus leaders, for example, TEV leader (Tobacco Etch Virus) (Gallie et al. (1995) *Gene* 165(2) :233–238); MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, imidazolinones, and 2,4-dichlorophenoxyacetate (2,4-D). See generally, Yarranton (1992) Curr. Opin. Biotech. 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) Topics Mol. Struc. Biol. 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 promoter and other constitutive promoters disclosed in WO 99/43838 and U.S. Pat. No. 6,072,050; the core CaMV $^{35}$S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611, herein incorporated by reference.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also WO 99/43819 published Sep. 9, 1999, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen Fusarium moniliforme (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIPI (Rohincier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced defensin expression within a particular plant tissue. Tissue-preferred promoters include Yamamoto et al. (1997) *Plant J.* 12(2):255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3): 1331–1341; Van Camp et al. (1996) *Plant Physiol.* 112(2) 525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

Leaf-specific promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20):9586–9590.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

The method of transformation/transfection is not critical to the instant invention. Various methods of transformation or transfection are currently available. As newer methods are available to transform crops or other host cells they may be used with the instant invention. Accordingly, a wide variety of methods have been developed to insert a DNA sequence into the genome of a host cell to obtain the transcription and/or translation of the sequence to effect phenotypic changes in the organism. The nucleic acid fragments of the instant invention may be used to create transgenic plants in which the disclosed plant defensin are present at higher or lower levels than normal or in cell types or developmental stages in which they are not normally found. This would have the effect of altering the level of disease (e.g., fungal) resistance and stress tolerance in those cells. Thus, any method, which provides for effective transformation/transfection may be employed.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) EMBO J. 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; McCabe et al. (1988) *Biotechnology* 6:923–926); and Lec1 transformation (WO 00/28058). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell*

4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago saliva*), rice (*Oryza sativa*), rye (*Secale cereale*), *sorghum* (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassaya (*Manihot esculenta*), coffee (Coffea spp.), coconut (*Cocos nucifera*), pineapple (*Ananas comosus*), citrus trees (Citrus spp.), *cocoa* (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), *macadamia* (*Macadamia integrifolia*), almond (*Prunus amygdalus*), sugar beets (*Beta vulgaris*), sugarcane (Saccharum spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp., Pisum spp.), and members of the genus *Cucumis* such as cucumber (*C. sativus*), cantaloupe (*C. cantalupensis*), and musk melon (*C. melo*). Ornamentals include azalea (Rhododendron spp.), hydrangea (*Hydrangea macrophylla*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived PL promoter and N-gene ribosome binding site (Simatake and Rosenberg (1981) *Nature* 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229–235 and Mosbach et al. (1983) *Nature* 302:543–545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention. Such antimicrobial proteins can be used for any application including coating surfaces to target microbes as described further infra.

Synthesis of heterologous nucleotide sequences in yeast is well known. Sherman, et al. (1982) *Methods in Yeast Genetics* (Cold Spring Harbor Laboratory) is a well recognized work describing the various methods available to produce proteins in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like, as desired.

A protein of the present invention, once expressed, can be isolated from yeast by lysing the cells and applying standard protein isolation techniques to the lysates. The monitoring of the purification process can be accomplished by using Western blot techniques, radioimmunoassay, or other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider (1987) *J. Embryol. Exp. Morphol.* 27:353–365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773–781). Additionally, gene sequences to control replication in the host cell may be incorporated into the vector such as those found in bovine papilloma virus type-vectors. Saveria-Campo (1985) "Bovine Papilloma Virus DNA a Eukaryotic Cloning Vector," in *DNA Cloning Vol. II. A Practical Approach*, ed. D. M. Glover (IRL Press, Arlington, Va.), pp. 213–238.

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art. Kuchler (1997) *Biochemical Methods in Cell Culture and Virology* (Dowden, Hutchinson and Ross, Inc.).

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.*100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one that allows large numbers of samples to be processed rapidly, since it will be expected that a large number of transformants will be negative for the desired phenotype.

The present invention also provides an isolated polypeptide selected from the group consisting of: a polypeptide comprising an amino acid sequence set forth in SEQ ID NO: 2, 4, 6, 8, 10, 12, 14, 16, 18, 20, 22, 24, 26, 28, 32, 47, or 49; a polypeptide characterized by at least 80% identity to SEQ ID NO: 6, 26, or 28; a polypeptide characterized by at least 85% identity to SEQ ID NO: 8; a polypeptide characterized by at least 95% identity to SEQ ID NO: 2, 4, 10, 12, 14, 16, 18, 20, 22, 24, or 47; a polypeptide characterized by at least 97% identity to SEQ ID NO: 32; and the polypeptide of SEQ ID NO: 49.

The instant polypeptides are useful in methods for impacting a plant pathogen comprising introducing into a plant or cell thereof at least one nucleotide construct comprising a nucleotide sequence of the invention operably linked to a promoter that drives expression of an operably linked sequence in plant cells, wherein said nucleotide sequence is selected from the group consisting of: a nucleotide sequence set forth in SEQ ID NO: 1, 3, 5, 7, 9, 11, 13, 15, 17, 19, 21, 23, 25, 27, 29, 31, 46, or 48; a nucleotide sequence that encodes a polypeptide having the amino acid sequence set forth in SEQ ID NO: 2, 4, 6, 8, 10, 12, 14, 16, 18, 20, 22, 24, 26, 28, 32, 47, or 49; a nucleotide sequence that encodes a mature polypeptide having the amino acid sequence set forth in SEQ ID NO: 35; a nucleotide sequence characterized by at least 75% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 80% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 85% sequence identity to the nucleotide sequence set forth in SEQ ID NO: 1, 3, 5, 7, 9, 11, 13, 15, 17, 19, 21, 23, 25, 27, 29, 31, 46, or 48; a nucleotide sequence characterized by at least 90% sequence identity to the nucleotide sequence set forth in SEQ ID NO: 1, 3, 5, 7, 9, 11, 13, 15, 17, 19, 21, 23, 25, 27, 29, 31, 46, or 48; and a nucleotide sequence that comprises the complement of any one of the above.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Polyclonal defensin-like antibodies can be prepared by immunizing a suitable subject (e.g., rabbit, goat, mouse, or other mammal) with an defensive agent immunogen. The anti-defensin antibody titer in the immunized subject can be monitored over time by standard techniques, such as with an enzyme linked immunosorbent assay (ELISA) using immobilized antimicrobial polypeptides. At an appropriate time after immunization, e.g., when the anti-defensive agent antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550–52; Kenneth (1980) in *Monoclonal Antibodies: A New Dimension In Biological Analyses* (Plenum Publishing Corp., New York); and Lerner (1981) *Yale J. Biol. Med.* 54:387–402).

Alternative to preparing monoclonal antibody-secreting hybridomas, a monoclonal anti-defensin-like antibody can be identified and isolated by screening a recombinant combinatorial immunoglobulin library (e.g., an antibody phage display library) with a defensin to thereby isolate immunoglobulin library members that bind the defensive agent. Kits for generating and screening phage display libraries are commercially available (e.g., the Pharmacia Recombinant Phage Antibody System, Catalog No. 27–9400–01; and the Stratagene SurfZAP™ Phage Display Kit, Catalog No. 240612). Additionally, examples of methods and reagents particularly amenable for use in generating and screening an antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734. The antibodies can be used to identify homologs of the defensins of the invention.

All or a substantial portion of the polynucleotides of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. in: *Nonmammalian Genomic Analysis: A Practical Guide*, Academic Press, New York), 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci. USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

Compositions and methods for controlling pathogenic agents are provided in the present invention. The anti-pathogenic compositions comprise plant defensin nucleotide and amino acid sequences. Particularly, the plant nucleic acid and amino acid sequences and fragments and variants thereof set forth herein possess anti-pathogenic activity. Accordingly, the compositions and methods are useful in protecting plants against fungal pathogens, viruses, nematodes, insects, and the like. Additionally provided are transformed plants, plant cells, plant tissues and seeds thereof.

By "plant pathogen" or "plant pest" any organism that can cause harm to a plant, by inhibiting or slowing the growth of a plant, by damaging the tissues of a plant, by weakening the immune system of a plant, reducing the resistance of a plant to abiotic stresses, and/or by causing the premature death of the plant, etc., is intended. Plant pathogens and plant pests include insects, nematodes, and organisms such as fungi, viruses, and bacteria.

By "disease resistance" or "pathogen resistance" it is intended that the organisms avoid the disease symptoms that are the outcome of organism-pathogen interactions. That is, pathogens are prevented from causing diseases and the associated disease symptoms, or alternatively, the disease symptoms caused by the pathogen is minimized or lessened.

By "anti-pathogenic compositions" it is intended that the compositions of the invention are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

An "antimicrobial agent," a "pesticidal agent," a "defensin," an "antiviral agent," an "insecticidal agent," and/or a "fungicidal agent" will act similarly to suppress, control, and/or kill the invading pathogen.

A defensive agent will possess defensive activity. By "defensive activity" an antipathogenic, antimicrobial, antiviral, insecticidal, or antifungal activity is intended.

By "antipathogenic compositions" it is intended that the compositions of the invention have activity against pathogens; including fungi, microorganisms, viruses, insects, and nematodes, and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect organisms, particularly plants, from disease, particularly those diseases that are caused by invading pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

In specific embodiments, methods for increasing pathogen resistance in a plant comprise stably transforming a plant with a DNA construct comprising an antipathogenic nucleotide sequence of the invention operably linked to a promoter that drives expression in a plant. Such methods find use in agriculture particularly in limiting the impact of plant pathogens on crop plants. While the choice of promoter will depend on the desired timing and location of expression of the anti-pathogenic nucleotide sequences, preferred promoters include constitutive and pathogen-inducible promoters.

It is understood in the art that plant DNA viruses and fungal pathogens remodel the control of the host replication and gene expression machinery to accomplish their own replication and effective infection. The present invention may be useful in preventing such corruption of the cell.

The defensin sequences find use in disrupting cellular function of plant pathogens or insect pests as well as altering the defense mechanisms of a host plant to enhance resistance to disease or insect pests. While the invention is not bound by any particular mechanism of action to enhance disease resistance, the gene products of the defensin sequences function to inhibit or prevent diseases in a plant.

The methods of the invention can be used with other methods available in the art for enhancing disease resistance in plants. For example, any one of a variety of second nucleotide sequences may be utilized, embodiments of the invention encompass those second nucleotide sequences that, when expressed in a plant, help to increase the resistance of a plant to pathogens. It is recognized that such second nucleotide sequences may be used in either the sense or antisense orientation depending on the desired outcome. Other plant defense proteins include those described in PCT patent publications WO 99/43823 and WO 99/43821, both of which are herein incorporated by reference.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* f.sp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium roltsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphamidermatum, Pythium ultimum, Pythium debaryanum*, Tomato spotted wilt virus, *Heterodera glycines, Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibacter Michigan's* subsp. *insidiosum, Pythium ultimum, Pythium irregulare, Pythium splendens, Pythium debaryanum, Pythium aphamidermatum, Phytophthora megasperma, Peronospora trifoliorum, Phoma medicaginis* var. *medicaginis, Cercospora medicaginis, Pseudopeziza medicaginis, Leptotrochila medicaginis*, Fusarium spp., *Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphamidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Tilletia indica, Pythium gramicola*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae* (*Fusarium graminearum*), *Stenocarpella maydis* (*Diplodia maydis*), *Pythium irregulare, Pythium debaryanum, Pythium graminicola, Pythium splendens, Pythium ultimum, Pythium aphamidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudomonas avenae, Erwinia chrysanthemi* p.v. *zea, Erwinia carotovora*, Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Periconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*),

*Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, and lesion nematodes, including Heterodera and Globodera spp.; particularly *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode). Additional nematodes include: *Heterodera cajani; Heterodera trifolii; Heterodera oryzae; Globodera tabacum; Meloidogyne incognita; Meloidogynejavonica; Meloidogyne hapla; Meloidogyne arenaria; Meloidogyne naasi; Meloidogyne exigua; Xiphinema index; Xiphinema italiae; Xiphinema americanum; Xiphinema diversicaudatum; Pratylenchus penetrans; Pratylenchus brachyurus; Pratylenchus zeae; Pratylenchus coffeae; Pratylenchus thornei; Pratylenchus scribneri; Pratylenchus vulnus; Pratylenchus curvitatus; Radopholus similis; Radopholus citrophilus; Ditylenchus dipsaci; Helicotylenchus multicintus; Rotylenchulus reniformis*; Belonolaimus spp.; *Paratrichodorus anemones*; Trichodorus spp.; Primitivus spp.; *Anguina tritici; Bider avenae; Subanguina radicicola*; Tylenchorhynchus spp.; *Haplolaimus seinhorsti; Tylenchulus semipenetrans; Hemicycliophora arenaria; Belonolaimus langicaudatus; Paratrichodorus xiphinema; Paratrichodorus christiei; Rhadinaphelenchus cocophilus; Paratrichodorus minor; Hoplolaimus galeatus; Hoplolaimus columbus*; Criconemella spp.; Paratylenchus spp.; *Nacoabbus aberrans; Aphelenchoides besseyi; Ditylenchus angustus*; Hirchmaniella spp.; Scutellonema spp.; *Hemicriconemoides kanayaensis; Tylenchorynchus claytoni*; and *Cacopaurus pestis.*

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blotch leafminer; *Anaphothrips obscrurus*, grass thrips; *Solenopsis milesta*, thief ant; *Tetranychus urticae*, twospotted spider mite; Sorghum: Chilopartellus, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes, migratory grasshopper; Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia spp., Root maggots.

The methods of the invention can be used with other methods available in the art for enhancing disease resistance in plants. Similarly, the antimicrobial compositions described herein may be used alone or in combination with other nucleotide sequences, polypeptides, or agents to protect against plant diseases and pathogens. Although any one of a variety of second nucleotide sequences may be utilized, specific embodiments of the invention encompass those second nucleotide sequences that, when expressed in a plant, help to increase the resistance of a plant to pathogens.

Proteins, peptides, and lysozymes that naturally occur in insects (Jaynes et al. (1987) *Bioassays* 6:263–270), plants (Broekaert et al. (1997) *Critical Reviews in Plant Sciences* 16:297–323), animals (Vunnam et al. (1997) *J. Peptide Res.* 49:59–66), and humans (Mitra and Zang (1994) *Plant Physiol.* 106:977–981; Nakajima et al. (1997) *Plant Cell Reports* 16:674–679) are also a potential source of plant disease resistance (Ko, K. (2000) www.scisoc.org/feature/BioTechnology/antimicrobial.html). Examples of such plant resistance-conferring sequences include those encoding sunflower rhoGTPase-Activating Protein (rhoGAP), lipoxygenase (LOX), Alcohol Dehydrogenase (ADH), and Sclerotinia-Inducible Protein-1 (SCIP-1) described in U.S. Pat. No. 6,709,865, herein incorporated by reference. These nucleotide sequences enhance plant disease resistance through the modulation of development, developmental pathways, and the plant pathogen defense system. Other plant defense proteins include those described in WO 99/43823 and WO 99/43821, all of which are herein incorporated by reference. It is recognized that such second nucleotide sequences may be used in either the sense or antisense orientation depending on the desired outcome.

In another embodiment, the defensins comprise isolated polypeptides of the invention. The defensins of the invention find use in the decontamination of plant pathogens during the processing of grain for animal or human food consumption; during the processing of feedstuffs, and during the processing of plant material for silage. In this embodiment, the defensins of the invention are presented to grain, plant material for silage, or a contaminated food crop, or during an appropriate stage of the processing procedure, in amounts effective for antimicrobial activity. The compositions can be applied to the environment of a plant pathogen by, for example, spraying, atomizing, dusting, scattering, coating or pouring, introducing into or on the soil, introducing into irrigation water, by seed treatment, or dusting at a time when the plant pathogen has begun to appear or before the appearance of pests as a protective measure. It is recognized that any means that bring the defensive agent polypeptides in contact with the plant pathogen can be used in the practice of the invention.

Additionally, the compositions can be used in formulations used for their antimicrobial activities. Methods are provided for controlling plant pathogens comprising applying a decontaminating amount of a polypeptide or composition of the invention to the environment of the plant pathogen. The polypeptides of the invention can be formulated with an acceptable carrier into a composition(s) that is, for example, a suspension, a solution, an emulsion, a dusting powder, a dispersible granule, a wettable powder, an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bacteriocides, nematocides, molluscicides, acaracides, plant growth regulators, harvest aids, and fertilizers, can be combined with carriers, surfactants, or adjuvants customarily employed in the art of formulation or other components to facilitate product handling and application for particular target mycotoxins. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds. In some embodiments, methods of applying an active ingredient of the present invention or an agrochemical composition of the present invention (which contains at least one of the proteins of the present invention) are foliar application, seed coating, and soil application.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g. polyoxyethylene sorbitar fatty acid esters, block copolymers of ethylene oxide and propylene oxide, acetylenic glycols such as 2, 4, 7, 9-tetraethyl-5-decyn-4,7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as a concentrate of a primary composition, which requires dilution with a suitable quantity of water or other diluent before application. The decontaminating concentration will vary depending upon the nature of the particular formulation, specifically, whether it is a concentrate or to be used directly.

In a further embodiment, the compositions, as well as the polypeptides of the present invention can be treated prior to formulation to prolong the activity when applied to the environment of a plant pathogen as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W. H. Freeman and Co.)).

In an embodiment of the invention, the compositions of the invention comprise a microbe having stably integrated the nucleotide sequence of a defensive agent. The resulting microbes can be processed and used as a microbial spray. Any suitable microorganism can be used for this purpose. See, for example, Gaertner et al. (1993) in *Advanced Engineered Pesticides*, Kim (Ed.). In one embodiment, the nucleotide sequences of the invention are introduced into microorganisms that multiply on plants (epiphytes) to deliver the defensins to potential target crops. Epiphytes can be, for example, gram-positive or gram-negative bacteria.

It is further recognized that whole, i.e., unlysed, cells of the transformed microorganism can be treated with reagents that prolong the activity of the polypeptide produced in the microorganism when the microorganism is applied to the environment of a target plant. A secretion signal sequence may be used in combination with the gene of interest such that the resulting enzyme is secreted outside the microorganism for presentation to the target plant.

In this manner, a gene encoding a defensive agent of the invention may be introduced via a suitable vector into a microbial host, and said transformed host applied to the environment, plants, or animals. Microorganism hosts that are known to occupy the "phytosphere" (phylloplane, phyllosphere, rhizosphere, and/or rhizoplane) of one or more crops of interest may be selected for transformation. These microorganisms are selected so as to be capable of successfully competing in the particular environment with the wild-type microorganisms, to provide for stable maintenance and expression of the gene expressing the detoxifying polypeptide, and for improved protection of the proteins of the invention from environmental degradation and inactivation.

Such microorganisms include bacteria, algae, and fungi. Illustrative prokaryotes, both Gram-negative and -positive, include *Enterobacteriaceae*, such as *Escherichia, Erwinia, Shigella, Salmonella*, and *Proteus; Bacillaceae; Rhizobiaceae*, such as *Rhizobium; Spirillaceae*, such as photobacterium, *Zymomonas, Serratia, Aeromonas, Vibrio, Desulfovibrio, Spirillum; Lactobacillaceae; Pseudomonadaceae*, such as *Pseudomonas* and *Acetobacter; Azotobacteraceae*; and *Nitrobacteraceae*. Among eukaryotes are fungi, such as *Phycomycetes* and *Ascomycetes*, which includes yeast, such as *Saccharomyces* and *Schizosaccharomyces*; and *Basidiomycetes yeast*, such as *Rhodotorula, Aureobasidium, Sporobolomyces*, and the like.

Of particlular interest are microorganisms, such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*; fungi, particularly yeast, e.g., *Saccharomyces, Pichia, Cryptococcus, Kluyveromyces, Sporobolomyces, Rhodotorula, Aureobasidium*, and *Gliocladium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pullulans*.

In an embodiment of the invention, the defensins of the invention may be used as a pharmaceutical compound for treatment of fungal and microbial pathogens in humans and other animals. Diseases and disorders caused by fungal and microbial pathogens include but are not limited to fungal meningoencephalitis, superficial fungal infections, ringworm, Athlete's foot, histoplasmosis, candidiasis, thrush, coccidioidoma, pulmonary cryptococcus, trichosporonosis, piedra, tinea nigra, fungal keratitis, onychomycosis, tinea capitis, chromomycosis, aspergillosis, endobronchial pulmonary aspergillosis, mucormycosis, chromoblastomycosis, dermatophytosis, tinea, fusariosis, pityriasis, mycetoma, pseudallescheriasis, and sporotrichosis.

In particular, the compositions of the invention may be used as pharmaceutical compounds to provide treatment for diseases and disorders associated with, but not limited to, the following fungal pathogens: *Histoplasma capsulatum, Candida spp.* (*C. albicans, C. tropicalis, C. parapsilosis, C. guilliermondii, C. glabrata/Torulopsis glabrata, C. krusei, C. lusitaniae*), *Aspergillus fumigatus, A. flavus, A. niger, Rhizopus spp., Rhizomucor spp., Cunninghamella spp., Apophysomyces spp., Saksenaee spp., Mucor spp.*, and *Absidia spp*. Efficacy of the compositions of the invention as anti-fungal treatments may be determined through anti-fungal assays known to one in the art.

The defensins may be administered to a patient through numerous means. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 μg/kg to about 20 mg/kg (e.g., 0.1 to 20 mg/kg) of active compound is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" comprises, but is not limited to, the small molecules, peptides, antibodies, and antisense oligonucleotides of the invention.

The defensins of the invention can be used for any application including coating surfaces to target microbes. In this manner, target microbes include human pathogens or microorganisms. Surfaces that might be coated with the defensins of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047 herein incorporated by reference.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various *Dimorphotheca sinuata, Picramnia pentandra, Parthenium argentatum* Grey, *Vernonia mespilifolia, Nicotiana benthamiana*, and *Helianthus annuus* tissues were prepared. The characteristics of the libraries are described below.

TABLE 2 cDNA Libraries from *Dimorphotheca sinuata, Picramnia pentandra, Parthenium argentatum* Grey, and *Nicotiana benthamiana*, Vernonia, and *Helianthus annuus*

| Library | Tissue | Clone |
|---|---|---|
| dms2c | African Daisy (*Dimorphotheca sinuata*) Developing Seed | dms2c.pk001.d3 |
| epb1c | *Parthenium argentatum* Grey Stem Bark | epb1c.pk001.h15<br>epb1c.pk002.h2<br>epb1c.pk003.p14<br>epb1c.pk004.p22<br>epb1c.pk005.o6<br>epb1c.pk006.k15 |
| epb3c | *Parthenium argentatum* Grey Stem Bark | epb3c.pk009.j22 |
| pps | Florida Bitterbush (*Picramnia pentandra*) Developing Seed | pps.pk0011.a9<br>pps.pk0010.g2 |
| tdr1c | *Nicotiana benthamiana* Developing Root | tdr1c.pk002.g7 |
| vs1n | Vernonia Seed* | vs1n.pk0009.h6<br>vs1n.pk007.a9 |
| hss1c | Sunflower plants (*Helianthus annuus*) infected with the plant fungus Sclerotinia | hss1c.pk018.k14 |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al. (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.), that is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding plant dofensin were identified by conducting BLAST (Basic Local Alignment Search Tool; Altschul et at. (1993) *J. Mol. Biol.* 215:403–410 searches for similarity to sequences contained in the BLAST "nr" database (comprising all non-redundant GenBank CDS translations1 sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266–272) provided by the NCBI. For convenience, the P-value (probability) or observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the GenBank database as described above. ESTs that contain sequences more 5' or 3' can be found by using the BLASTn algorithm (Altschul et al. (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5' or 3' direction. Once the most 5' EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Plant Defensin

The BLASTX search using the EST sequences from clones dms2c.pk001.d3, epb1c.pk002.h2, pps.pk0011.a9 revealed similarity of the proteins encoded by the cDNAs to defensin from *Dahlia merckii* (NCBI GenBank Identifier (GI) No. 2147320). The BLAST results for each of these ESTs are shown in Table 3:

TABLE 3

BLAST Results for Clones Encoding Polypeptides Homologous to Plant Defensin

| Clone | BLAST pLog Score 2147320 |
|---|---|
| dms2c.pk001.d3 | 30.4 |
| epb1c.pk002.h2 | 30.3 |
| pps.pk0011.a9 | 24.0 |

The BLASTX search using the EST sequence from clone tdr1c.pk002.g7 revealed similarity of the protein encoded by the cDNA to defensin from *Nicotiana tabacum* (NCBI GI No. 676882) with a pLog value of 16.4.

The sequence of a portion of the cDNA insert from clone dms2c.pk001.d3 is shown in SEQ ID NO: 1; the deduced amino acid sequence of this cDNA is shown in SEQ ID NO:2. The sequence of a portion of the cDNA insert from clone epb1c.pk002.h2 is shown in SEQ ID NO:9; the deduced amino acid sequence of this cDNA is shown in SEQ ID NO: 10. The sequence of a portion of the cDNA insert from clone pps.pk0011.a9 is shown in SEQ ID NO:5; the deduced amino acid sequence of this cDNA is shown in SEQ ID NO:6. The sequence of a portion of the cDNA insert from clone tdr1c.pk002.g7 is shown in SEQ ID NO:25; the deduced amino acid sequence of this cDNA is shown in SEQ ID NO:26. BLAST scores and probabilities indicate that the instant nucleic acid fragments encode portions of plant defensins. These sequences represent the first sequences encoding defensin from African daisy (*Dimorphotheca sinuata*), Parthenium (*Parthenium argentatum* Grey), Florida bitterbush (*Picramnia pentandra*), and tobacco (*Nicotiana benthamiana*).

The BLASTX search using the EST sequences from clones listed in Table 4 revealed similarity of the polypeptides encoded by the cDNAs to a defensin from *Dahlia merckii* (NCBI GenBank Identifier (GI) No. 2147320; WO 99/02038-A1; Osborn et al. (1995) *FEBS Lett.* 368:257–262). Shown in Table 4 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding at a minimum the entire mature protein derived from an EST, an FIS, a contig, or an FIS and PCR ("CGS"):

TABLE 4

BLAST Results for Sequences Encoding Polypeptides Homologous to Plant Defensin

| Clone | Status | BLAST pLog Score 2147320 |
|---|---|---|
| dms2c.pk001.d3(FIS) | CGS | 25.70 |
| pps.pk0011.a9(FIS) | CGS | 23.10 |
| epb1c.pk002.h2(FIS) | CGS | 25.22 |
| epb1c.pk001.h15(EST) | CGS | 25.00 |
| epb1c.pk003.p14(EST) | CGS | 30.22 |
| epb1c.pk004.p22(EST) | CGS | 30.22 |
| epb1c.pk005.o6(EST) | CGS | 30.22 |
| epb1c.pk006.k15(EST) | CGS | 30.22 |
| epb3c.pk009.j22(EST) | CGS | 30.22 |
| tdr1c.pk002.g7(FIS) | CGS | 11.70 |
| pps.pk0010.g2(FIS) | CGS | 23.10 |
| vs1n.pk0009.h6(FIS) | CGS | 27.05 |

The data in Table 5 represents a calculation of the percent identity of the amino acid sequence set forth in SEQ ID NSs:4, 8, 12, 14, 16, 18, 20, 22, 24, 28, 30, and 32, and the *Dahlia merckii* sequence (NCBI GenBank Identifier (GI) No. 2147320; SEQ ID NO:33).

TABLE 5

Percent Identity of Amino Acid Sequences Deduced From the Nucleotide Sequences of cDNA Clones Encoding Polypeptides Homologous to Plant Defensin

| SEQ ID NO. | Percent Identity to NCBI GenBank Identifier (GI) No. 2147320; SEQ ID NO:33 |
|---|---|
| 4 | 92.0 |
| 8 | 84.0 |
| 12 | 92.0 |
| 14 | 92.0 |
| 16 | 92.0 |
| 18 | 92.0 |
| 20 | 92.0 |
| 22 | 92.0 |
| 24 | 92.0 |
| 28 | 56.0 |
| 30 | 84.0 |
| 32 | 96.0 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire plant defensins. These sequences represent the first African daisy (*Dimorphotheca sinuata*), *Parthenium* (*Parthenium argentatum* Grey), Florida bitterbush (*Picramnia pentandra*), tobacco (*Nicotiana benthamiana*), and *Vernonia mespilifolia* sequences encoding plant defensin known to Applicants.

Sequence alignments and percent identity calculations were also performed using the GAP program in the Wisconsin Genetics Software package, Version 10.0 (available from Genetics Computer Group, 575 Science Drive, Madison, Wis., USA). The *Dahlia merkii* sequence (NCBI GenBank Identifier (GI) No. 2147320; SEQ ID NO: 33) was compared to SEQ ID NOS: 47 and 49 using the GAP program, and the percent identity values obtained are shown in Table 6.

TABLE 6

Percent Identity of Amino Acid Sequences Deduced From the Nucleotide Sequences of cDNA Clones Encoding Polypeptides Homologous to Plant Defensin

| SEQ ID NO. | Percent Identity to NCBI GenBank Identifier (GI) No. 2147320; SEQ ID NO:33 |
|---|---|
| 47 | 92.0 |
| 49 | 98.0 |

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, is constructed. The cDNA fragment of this gene is generated by polymerase chain reaction (PCR) of the cDNA clone using appropriate oligonucleotide primers. Cloning sites (NcoI or SmaI) are incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band is isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA is ligated at 15° C. overnight, essentially as described (Maniatis). The ligated DNA is then used to transform *E. coli* XL1-Blue (Epicurian *Coli XL*-1 Blue™; Stratagene). Bacterial transformants are screened by restriction enzyme digestion of plasmid DNA and limited nucleotide sequence analysis using the dideoxy chain termination method (Sequenase T DNA Sequencing Kit; U.S. Biochemical). The resulting plasmid construct comprises a chimeric gene encoding, in the 5' to 3' direction, the maize 27 kD zein promoter, a cDNA fragment encoding the instant polypeptide, and the 10 kD zein 3'region.

The chimeric gene described above is then introduced into corn cells by the following procedure. Immature corn embryos are dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant is cultured on N6 medium and sub-cultured on this medium every 2 to 3 weeks.

The plasmid, p35S/Ac (obtained from Dr. Peter Eckes, Hoechst Ag, Frankfurt, Germany) is used in transformation experiments in order to provide for a selectable marker. This plasmid contains the Pat gene (see European Patent Publication 0 242 236) that encodes phosphinothricin acetyl transferase (PAT). The enzyme PAT confers resistance to herbicidal glutamine synthetase inhibitors such as phosphinothricin. The Pat gene in p35S/Ac is under the control of the $^{35}$S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens.*

The particle bombardment method (Klein et al. (1987) *Nature* 327:70–73) is used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles is then placed in the center of a Kapton™ flying disc (Bio-Rad Labs). The particles are then accelerated into the corn tissue with a Biolistic™ PDS-1000/He instrument (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and coveres a circular area of about 5 cm in diameter. The petri dish containing the tissue is placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue is transferred to N6 medium that contains glufosinate (2 mg per liter) and lacks casein or proline. The tissue continues to grow slowly on this medium. After an additional 2 weeks the tissue is transferred to fresh N6 medium containing glufosinate. After 6 weeks, areas of about 1 cm in diameter of actively growing callus is identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) is used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites are incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos are then transformed with the expression vector comprising sequences encoding the instant polypeptides. To induce somatic embryos, cotyledons, 3–5 mm in length dissected from surface sterilized, immature seeds of the soybean cultivar A2872, are cultured in the light or dark at 26° C. on an appropriate agar medium for 6–10 weeks. Somatic embryos that produce secondary embryos are then excised and placed into a suitable liquid medium. After repeated selection for clusters of somatic embryos that multiplied as early, globular staged embryos, the suspensions are maintained as described below.

Soybean embryogenic suspension cultures are maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures are then transformed by the method of particle gun bombardment (Klein et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the $^{35}$S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment is then inserted into a unique restriction site of the vector carrying the marker gene.

To 50 μL of a 60 mg/mL 1 μm (in diameter) gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension is sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette.

For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue is divided in half and placed back into liquid and cultured as described above.

Five to seven days post bombardment, the liquid media is exchanged with fresh media, and eleven to twelve days post bombardment with fresh media containing 50 nig/mL hygromycin. This selective media is refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line is treated as an independent transformation event. These suspensions are then subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135), that employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA is appropriately digested to release a nucleic acid fragment encoding the protein. This fragment is then purified on a 1% NuSieve GTG™ low melting agarose gel (FMC). Buffer and agarose contain 10 μg/ml ethidium bromide for visualization of the DNA fragment. The fragment is then purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters is purified from the excess adapters using low melting agarose as described above. The vector pBT430 is digested, dephosphorylated with alkaline phosphatase (NEB) and deproteinized with phenol/chloroform as described above. The prepared vector pBT430 and fragment is then ligated at 16° C. for 15 hours followed by transformation into DH5 electrocompetent cells (GIBCO BRL). Transformants are selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads are added and the mixture sonicated 3 times for about 5 seconds each time with a microprobe sonicator. The mixture is centrifuged and the protein concentration of the supernatant determined. One μg of protein from the soluble fraction of the culture is separated by SDS-polyacrylamide gel electrophoresis. Gels are observed for protein bands migrating at the expected molecular weight.

Example 7

Assaying Plant Defensin Activity

The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin that is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiols. The eluted fusion protein may be subjected to further purification by traditional means as stated above, if desired. Proteolytic cleavage of the thioredoxin fusion protein and the enzyme may be accomplished after the fusion protein is purified or while the protein is still bound to a ThioBond™ affinity resin (Invitrogen Corporation, Carlsbad, Calif.) or other resin.

Crude, partially purified or purified enzyme, either alone or as a fusion protein, may be utilized in assays to verify over- or underexpression of functional plant defensins in transgenic plants and transformed bacterial cells. Assays may be conducted under well known experimental conditions which permit optimal enzymatic activity. For example, assays for plant defensin are presented by Thevissen et al. (1996) *J. Biol. Chem.* 271(25):15018–15025.

Example 8

Cloning of the Mature Peptide of the *Picramnia pentandra* Defensin Clone pps.pk0010.g2 (Pps-AMP1) into an *E.coli*. Expression Vector The nucleotide and amino acid sequences corresponding to the mature peptide of clone pps.pk0010.g2, also known as Pps-AMP1 (SEQ ID NO:30), is shown below (mature sequences are set forth in SEQ ID NOS: 34 and 35).

```
      Q  R  L  C   E  R  A   S  L  T  W  S  G  N   C  G  N •
    1 CAAAGACTAT GTGAAAGAGC AAGCTTAACA TGGTCAGGCA ATTGTGGCAA
      GTTTCTGATA CACTTTCTCG TTCGAATTGT ACCAGTCCGT TAACACCGTT

     • T  A  H   C  D  N  Q   C  R  S   W  E  H   A  Q  H  G •
   51 CACTGCTCAC TGTGACAACC AGTGTAGGTC ATGGGAGCAC GCACAACACG
      GTGACGAGTG ACACTGTTGG TCACATCCAG TACCCTCGTG CGTGTTGTGC

     •  A  C  H   V  R  G   G  K  H  M   C  F  C   Y  F  N
  101 GAGCATGTCA CGTACGAGGT GGAAAACATA TGTGCTTCTG CTACTTCAAT
      CTCGTACAGT GCATGCTCCA CCTTTTGTAT ACACGAAGAC GATGAAGTTA

       C  *
  151 TGCTGA
      ACGACT
```

The nucleotide sequence encoding the mature peptide of Pps-AMP1 is set forth in SEQ ID NO:34. The nucleotide sequence (SEQ ID NO: 34) was PCR amplified from its corresponding cDNA clone, pps.pk0010.g2 (see Table 1). The 5' PCR primer incorporated an extra ATG sequence corresponding to a methionine residue immediately upstream of the mature peptide coding sequence for expression in bacteria. The 5' and 3' PCR primers were also designed to incorporate an NdeI and BamHI site, respectively, to facilitate cloning into the expression plasmid pET12a (Novagen, Madison Wis.). The resulting PCR product was TOPO-cloned into pCR2.1 (Invitrogen, Carlsbad, Calif.) and sequence verified. A NdeI-BamHI fragment containing the Pps-AMP1 nucleotide sequence corresponding to the mature Pps-AMP1 peptide, with the added methionine residue, was subcloned from pCR2.1 into the corresponding sites of pET12a placing the Pps-AMP1 nucleotide sequence encoding for the mature peptide under control of the T7 promoter. The pET12a-PpsAMP1 construct was transformed into a compatible expression host, BL21 (DE3, pLysS) (Invitrogen) or Origami (DE3, pLysS) (Novagen) and expression of the mature Pps-AMP1 peptide was induced by addition of IPTG as described in Example 6.

Example 9

Induction and Expression of the Pps-AMP1 Mature Peptide (SEQ ID NO: 35)

Expression of the Pps-AMP1 mature peptide (SEQ ID NO: 35) was induced using the following protocol. 1 liter (L) of LB broth (with 500 μg/ml Carbenicillin and 34 μg/ml Chloramphenicol) was inoculated with 5 mls of an overnight culture (containing the same concentration of antibiotics) derived from a single isolated colony of BL21- or Origami-transformed cells (from Example 8). The culture was incubated at 37° C. with vigorous shaking (225 rpm) until an $OD_{600}$ between 0.6–0.7 was reached. IPTG (isopropryl-B-D-galactopyranoside) was added to the culture to a final concentration of 0.5 mM and the culture further incubated overnight at 37° C. The next day Pps-AMP1 mature peptide expression was confirmed by the presence of inclusion bodies in the bacteria under 1000× (oil emersion) magnification using a phase contrast light microscope.

The induced bacteria were pelleted by centrifugation (15,000 rpm for 10 min) and the pellet resuspended in 30 ml of 20 mM Tris-HCl (pH 7.5). The bacteria were lysed by French press at an equivalent cell pressure of 20,000 psi. The suspension was centrifuged at 15,000 rpm for 15 minutes to pellet inclusion bodies. Inclusion bodies were washed 2× with 100 ml of 20 mM Tris-HCl, pH 7.5, 10 mM EDTA, 1% Triton X-100.

Example 10

Refolding and Purification of the Pps-AMP1 Mature Peptide (SEQ ID NO: 35)

Inclusion bodies from Example 9 were resuspended in 6 M Guanidine hydrochloride, 0.1 M Tris-HCl, pH 8.0, 1 mM EDTA, and 0.1 M dithiothreitol. After shaking for two hours at low speed on an orbital shaker at room temperature, any remaining particulate matter was removed by centrifugation or filtration.

The solubilized protein was precipitated by addition of 6 volumes of ice cold acidic acetone (39:1 acetone:1 M HCl). The suspension was allowed to sit on ice for about 1 hour and then centrifuged at 2000 g for 6–8 minutes to pellet the protein. The pellet was washed twice with acidic acetone and allowed to air dry for 10 minutes before resolubilization in deionized water.

The unfolded protein was purified by reverse phase chromatography on a Vydac™ C 18 column (10 micron particle, 300 Angstrom pore size, Part number 218TP101510, Grace Vydac, Calif.) using a two step gradient consisting of Solvent A (95% $H_2O$, 5% acetonitrile, 0.1% trifluoroacetic acid) and Solvent B (5% $H_2O$, 95% acetonitrile, 0.1% trifluoroacetic acid). The first step of the gradient was 10% to 24% Solvent B at a flow rate of 3 ml/min for 3 min. The second step was from 24% to 40% Solvent B at a flow rate of 3 ml/min for 14 minutes. The protein was monitored by absorbance at 214 nm. Prior to loading on the column, the sample was adjusted to 1% trifluoroacetic acid and any precipitated material removed by centrifugation. The unfolded, reduced Pps-AMP1 mature peptide eluted at approximately 37% solvent B. Fractions corresponding to the unfolded peak of Pps-AMP1 mature protein were pooled and the protein concentration adjusted to 0.1 mg/mL-0.5 mg/mL by addition of 40% acetonitrile. The solution was brought to 0.1 M ammonium acetate, pH 6–9, and 1.0 mM reduced glutathione and stirred at room temperature until the Pps-AMP1 mature peptide was completely folded as determined by LC/MS analysis. Generally 24 hours was found to be sufficient for complete folding. Folded Pps-AMP1 mature peptide was purified by reverse phase chromatography on a Vydac™ C18 column (10 micron particle, 300 Angstrom pore size, Part number 218TP101510). The protein was eluted with a linear gradient (Solvent A-95% H2O, 5% acetonitrile and 0.1% trifluoroacetic acid, Solvent B—5% H2O, 95% acetonitrile, 0.1% trifluoroacetic acid) from 10% to 60% Solvent B in 45 minutes at 3 ml/min and monitored by absorbance at 214 run. Pure, folded Pps-AMP1 mature peptide was collected and freeze-dried. The freeze-dried protein can be resolubilized in water and a protein assay performed to determine concentration prior to bioassay.

Example 11

Bioactivity of Pps-AMP1 Mature Peptide Against Fungal Pathogens

The purified refolded and lyophilized Pps-AMP1 mature peptide was resuspended in $dH_2O$ to a final concentration of about 4 μg/μl. 12 μg of purified Pps-AMP1 mature peptide was added to 200 μl of ½ strength potato dextrose broth (PDB) containing a spore suspension of either *Fusarium verticilloides, Colletotrichum graminaria*, or *Neurospora crassa* containing 2500 spores/ml. This resulted in a stock solution with a starting concentration of 10 μM. A 0.5× dilution series for Pps-AMP1 mature peptide from 10 μM through to about 0.005 μM was prepared by removing 100 μl of the 10 μM stock and adding it to 100 μl of spore suspension (2500 spores/ml), mixing thoroughly to achieve a 5 μM Pps-AMP1 mature peptide concentration, transferring 100 μl of the 5 μM suspension to a fresh 100 μl spore suspension etc., until about 0.005 μM was reached. Two replicates per pathogen were performed. The fungal assay plate was scored for inhibition of fungal growth after a 48 hour incubation at 28° C. Inhibition of fungal growth was defined as little to no spore germination without detectable hyphae growth.

The bioactivity of Pps-AMP1 mature peptide against these fungal pathogens is shown below. The IC90 concentration represents that concentration at which 90% of fungal growth is inhibited.

| Fungus | IC90 (μM) |
|---|---|
| Colletotrichum | 2.5 |
| Fusarium | 0.6 |
| Neurospora | 0.05 |

An in vitro assay was also performed in a 96 well microtiter plate to determine the activity of Pps-AMP1 mature peptide against *Sclerotinia sclerotiorum*. Test inoculum was started by inoculating/2 strength potato dextrose broth (PDB) liquid with a sterile loop of hyphae from a Sclerotinia culture propagated on ⅛ strength potato dextrose agar (PDA) plate. Liquid inoculum was held at room temperature (22° C.), without shaking, in the dark for 4 days, to allow sufficient growth of hyphae. The resulting suspension was macerated using a polytron tissue grinder. The sample was then diluted to the point of invisibility to the naked eye (observation under microscopy at 40× indicated the presence of hyphal fragments). Serial dilutions of Pps-AMP1 mature peptide in fungal suspensions ranging from 10 μM to 0.005 μM were prepared as indicated above. As a positive control for this assay the fungal standard MBC (methyl 2-benzimidazolecarbamate) was formulated by adding 1 μl of each stock solution (in DMSO) to 99 μl of inoculum to achieve the following rates: 17, 5.67, 1.89, 0.63, 0.21, 0.07, 0.023, 0.008 μM. *Scierotinia* hyphae only, or ½ strength PDB only, were included as negative controls. Activity was demonstrated by inhibition of hyphal growth after 24 hours at 22° C.

The results are as follows:

1) PpsAmp1 mature peptide—(2 replicates)

10 μM—total inhibition of fungal growth.

5 μM—moderate inhibiton of fungal growth.

2.5 μM—0.005 μM no inhibition of fungal growth.

2) MBC standard—(2 replicates)

17—0.07 μM—total inhibition of fungal growth.

0.023 μM—moderate inhibition of fungal growth.

3) Inoculum control—(2 replicates)

Extensive fungal growth.

4) Media control—(2 replicates)

No contamination.

Example 12

Construction of Soybean Transformation Vectors

A synthetic version of Pps-AMP1 mature peptide (SEQ ID NQ:35) operably linked to a modified barley alpha amylase (BAA) signal peptide (SEQ ID NO: 50) (Rahmatullah R et at. (1989) *Plant Mol. Biol.* 12(1) :119–121) was constructed with a codon-bias representative of *Glycine max* (see SEQ ID NO: 36 for the synthetic nucleotide molecule comprising the BAA signal peptide operatively linked to the Pps-AMP1 mature peptide and SEQ ID NO: 37 (or the protein sequence corresponding to SEQ ID NO: 36). Codon usage based on *Glycine max* was chosen to maximize the expression of Pps-AMP1 mature peptide in soybean plants. The codon preference selected for the Pps-AMP1 mature peptide as well as the BAA signal sequence was derived from the codon usage database available from the website of the Kazusa DNA Research Institute. 2-6-7 Kazusa-kamatari, Kisarazu, Chiba 292-0812, Japan. See also Table 7. The BAA signal sequence was added to the Pps-AMP1 mature peptide coding sequence to facilitate the export Pps-AMP1 mature peptide out of the cell and into the intercellular space.

The synthetic gene was constructed using a series of overlapping complementary oligonucleotides that were annealed together, Klenow treated to repair the gaps, and PCR amplified using primers corresponding to 5' and 3' ends of the synthetic gene. XhoI and KpnI/NcoI sites were incorporated into the PCR primers to facilitate gene cloning. The PCR product was TOPO cloned into pCR2.1 (Invitrogen) and sequence verified. A XhoI-KpnI or a XhoI-NcoI fragment containing BAA-Pps-AMP1 mature peptide was subcloned into the corresponding sites of vectors containing either the soybean isoflavone synthetase 1 (IFS1) promoter (see U.S. Ser. No. 10/104,706) or the UBI1ZM-enhancer Rsyn7-syn core (UCP1) promoter (see U.S. Pat. No. 6,072,050 and U.S. Ser. No. 60/329,667). This placed BAA-mature Pps-AMP1 behind these two promoters with a 3' sequence corresponding to either the NOS or pin II (potato proteinase inhibitor gene; see Ryan (1990) *Ann. Rev. Phy-*

*topath.* 28:425–449 and Duan et al. (1996) *Nature Biotechnology* 14:494–498) terminator sequences. IFS1 is a strong constitutive root promoter that is also stress-inducible in aerial portions of the plant. The UCP1 promoter is a constitutive promoter that is SCN-inducible. Expression of Pps-AMP1 mature peptide either constitutively or inducibly in root tissue was desirable to test its effect on SCN. Furthermore, the inducibility of the IFS1 promoter due to stress also made this promoter suitable to direct expression of Pps-AMP1 mature peptide in tissues susceptible to Sclerotinia infection.

TABLE 7

| Glycine max [gbpln]: 619 CDS's (241657 codons) fields: [triplet] [frequency: per thousand] ([number]) | | | | | | | | | | | |
|---|---|---|---|---|---|---|---|---|---|---|---|
| UUU | 20.5 | (4964) | UCU | 17.5 | (4238) | UAU | 15.8 | (3808) | UGU | 7.2 | (1748) |
| UUC | 21.0 | (5067) | UCC | 12.2 | (2949) | UAC | 15.2 | (3667) | UGC | 7.5 | (1821) |
| UUA | 8.4 | (2030) | UCA | 14.9 | (3590) | UAA | 1.1 | (256) | UGA | 0.9 | (221) |
| UUG | 22.1 | (5343) | UCG | 4.6 | (1107) | UAG | 0.6 | (143) | UGG | 11.9 | (2866) |
| CUU | 23.5 | (5676) | CCU | 19.8 | (4794) | CAU | 13.5 | (3254) | CGU | 7.0 | (1697) |
| CUC | 16.8 | (4053) | CCC | 10.1 | (2445) | CAC | 10.9 | (2630) | CGC | 6.4 | (1538) |
| CUA | 8.1 | (1962) | CCA | 20.2 | (4875) | CAA | 20.5 | (4964) | CGA | 4.0 | (964) |
| CUG | 12.0 | (2900) | CCG | 4.2 | (1022) | CAG | 17.2 | (4147) | CGG | 2.8 | (683) |
| AUU | 26.0 | (6275) | ACU | 17.5 | (4231) | AAU | 21.2 | (5132) | AGU | 12.1 | (2935) |
| AUC | 16.5 | (3981) | ACC | 14.7 | (3562) | AAC | 22.9 | (5524) | AGC | 10.9 | (2640) |
| AUA | 12.8 | (3086) | ACA | 14.9 | (3601) | AAA | 26.4 | (6370) | AGA | 14.3 | (3459) |
| AUG | 22.4 | (5404) | ACG | 4.2 | (1006) | AAG | 37.5 | (9052) | AGG | 13.3 | (3218) |
| GUU | 26.7 | (6455) | GCU | 28.1 | (6796) | GAU | 32.9 | (7955) | GGU | 21.7 | (5248) |
| GUC | 12.3 | (2971) | GCC | 16.7 | (4042) | GAC | 20.4 | (4931) | GGC | 13.8 | (3339) |
| GUA | 7.3 | (1768) | GCA | 22.4 | (5421) | GAA | 33.9 | (8194) | GGA | 22.5 | (5434) |
| GUG | 22.1 | (5342) | GCG | 6.1 | (1470) | GAG | 34.3 | (8296) | GGG | 12.8 | (3097) |

Coding GC 46.16% 1st letter GC 53.12% 2nd letter GC 39.75% 3rd letter GC 45.62%

Example 14

Soybean Embryo Transformation

Soybean embryos were bombarded with a plasmid containing the Pps-AMP1 mature peptide encoding nucleotide sequence operably linked to either the IFS1 or UCP1 promoters as follows; somatic embryos derived from cotyledons less than 4 mm in length, dissected from surface-sterilized, immature seeds of the soybean cultivar Jack, were cultured in the light or dark at 26° C. on an appropriate agar medium for six to ten weeks. Somatic embryos producing secondary embryos were excised and placed into a suitable liquid medium. After repeated selection for clusters of somatic embryos that multiplied as early, globular-staged embryos, the suspensions were maintained as described below.

Soybean embryogenic suspension cultures were maintained in 35 ml liquid media on a rotary shaker at 150 rpm and 26° C. with fluorescent lights on a 16:8 hour day/night schedule. Cultures were subcultured every two weeks by inoculating approximately 35 mg of tissue into 35 ml of liquid medium.

Soybean embryogenic suspension cultures were then used for transformation experiments by the method of particle gun bombardment (Klein et al. (1987) *Nature* (London) 327:70–73, U.S. Pat. No. 4,945,050). A DuPont® Biolistic PDS1000®/HE instrument (helium retrofit) was used for these transformations.

A selectable marker expression cassette that can be used to facilitate soybean transformation comprises the $^{35}$S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase (NOS) gene from the T-DNA of the Ti plasmid of *Agrobacterium tumefaciens*. The expression cassette comprising the nucleotide sequence encoding the Pps-AMP1 mature peptide operably linked to a promoter can be isolated as a restriction fragment. This fragment is then inserted into a unique restriction site of the vector carrying the marker gene.

To 50 μl of a 60 mg/ml 1 μm (in diameter) gold particle suspension was added (in order): 5 μl DNA (1 μg/μl), 20 μl spermidine (0.1 M), and 50 μl $CaCl_2$ (2.5 M). The particle preparation was then agitated for three minutes, spun in a microfuge for 10 seconds and the supernatant removed. The DNA-coated particles were then washed once in 400 μl 70% ethanol and resuspended in 40 μl of anhydrous ethanol. The DNA/particle suspension was sonicated three times for one second each. Five microliters of the DNA-coated gold particles were then loaded on each macro carrier disk.

Approximately 300–400 mg of a two-week-old suspension culture was placed in an empty 60×15 mm Petri dish and the residual liquid removed from the tissue with a pipette. For each transformation experiment, approximately 5–10 plates of tissue are normally bombarded. Membrane rupture pressure was set at 1100 psi, and the chamber was evacuated to a vacuum of 28 inches mercury. The tissue was placed approximately 3.5 inches away from the retaining screen and bombarded three times. Following bombardment, the tissue was divided in half and placed back into liquid and cultured as described above.

Five to seven days post bombardment, the liquid media was exchanged with fresh media, and eleven to twelve days post-bombardment with fresh media containing 50 mg/ml hygromycin. This selective media was refreshed weekly. Seven to eight weeks post-bombardment, green, transformed tissue was observed growing from untransformed, necrotic embryogenic clusters. Isolated green tissue was removed and inoculated into individual flasks to generate new, clonally propagated, transformed embryogenic suspension cultures. Each new line was treated as an independent transformation event. These suspensions were then subcultured and maintained as clusters of immature embryos or regenerated into whole plants by maturation and germination of individual somatic embryos.

Example 15

DNA Preparation and PCR of Pps-AMP1 Events

The presence of the nucleotide sequence encoding the Pps-AMP1 mature peptide was confirmed in transgenic soybean events by PCR amplification. Genomic DNA was prepared from callus by shaking approximately 100 μl of callus at 1500 strokes/minute for 45 seconds in the Geno/Grinder in the presence of 1 steel ball (5/32"), 300 μl of urea extraction buffer and 300 μl of phenol/chloroform/isoamyl alcohol (25:24:1). Tubes were centrifuged at full speed for 5 minutes and 200 μl of the aqueous phase transferred to a 96 deep well block. DNA was precipitated with an equal volume of isopropanol, centrifuged at full speed for 10 minutes, and the DNA pellets washed with 70% ethanol. After a further 5 minute centrifugation the supernatant was removed completely and the pellets dried in a speed vacuum. The DNA was resuspended in 100 μl of 10 mM Tris HCL pH 8 and 2 μl used for PCR amplification.

PCR amplification was performed in a 96 well format using two sets of primers corresponding to the promoter/5' junction and the 3'/terminator junction. The primer names and sequences are as follows:

```
BAA1;
5'-GCTCGAGATGGCCAACAAGCATC-3';    SEQ ID NO:38

BAA2;
5'-CACATGTGTTTGCCTCCTCTAACG-3';   SEQ ID NO:39

UCP1-1;
5'-TCCACTCGAGCGGCTATAAATACG-3';   SEQ ID NO:40

IFS1-P1;
5'-CTTTGCGTCCTTGAAAAGTCCATG-3';   SEQ ID NO:41

PIN2;
5'-GGCCAATCCAGAAGATGGACAAGT-3';   SEQ ID NO:42

NOS1;
5'-CGCAAGACCGGCAACAGGATTC-3';     SEQ ID NO:43
```

For events containing IFS1:BAA-mature Pps-AMP1; primer pairs BAA2 (SEQ ID NO: 39)/IFS1-P1 (SEQ ID NO:41) and BAA1 (SEQ ID NO:38)/NOS1 (SEQ ID NO:43) were used. Events containing UCP1:BAA-mature Pps-AMP1 were PCR confirmed with the primer pairs BAA2 (SEQ ID NO:39)/UCP1-1 (SEQ ID NO:40) and BAA1 (SEQ ID NO:38)/PIN2 (SEQ ID NO:42).

PCR reactions contained 2 μl of genomic DNA preparation, 10 μl of ReadyTaq mix (Sigma), 0.5 μl of each primer (10 μM) of the primer pair in a total of reaction volume of 20 μl. PCR reactions were performed using one cycle of 95° C. for 5 min, 40 cycles of 95° C. 30 sec, 60° C. 1 min, 72° C. 1 min, and 1 cycle of 72° C. for 5 min. PCR products of the correct size were detected on a 1% agarose gel. Greater than 95% of the events showed PCR products corresponding to the predicted size for both primer pairs indicating that the events tested contained the expected construct.

Example 16

RT-PCR of IFS1 BAA-Mature Pps-AMP1 Events

Total RNA was extracted from a subset of IFS1:BAA-mature Pps-AMP1 events by collecting one leaflet per event into a 2 ml sterile screw cap tube, adding 2 steel balls (5/32"), and 1.0 ml of Trizol Reagent (GIBCO-BRL). Leaflets were homogenized in a DNA FastPrep instrument at a speed of 4.5 for 45 seconds and the tubes centrifuged for 10 min at 4° C. The supernatant was extracted with chloroform and the RNA precipitated from the aqueous phase with cold isopropyl alcohol. After a 10 minute centrifugation step the pellet was washed with 70% ethanol and dried in a speed vacuum. The pellet was resuspended in 90 μl of DEPC-treated $H_2O$ and amplification grade DNAseI (1 U) and 10× DNAse I buffer added to a total volume of 100 μl. The reaction was incubated at 37° C. for 15 min, twice extracted with an equal volume of phenol/chloroform/isoamyl alcohol and the RNA precipitated from the aqueous phase with 0.1 volume 3 M sodium acetate and 2.5 volume of 100% ethanol. After centrifugation the pellet was resuspended in 30 μl of DEPC-$H_2O$. RNA samples were stored at −80° C. until use.

RT-PCR amplification of the Pps-AMP1 mRNA was performed using the One-Step RT-PCR kit (GIBCO-BRL) and the gene specific primers named IFS1:BAA-mature Pps PCR1 (5'-CCCGGGCTCGAGATGGCCAACAAGCATC TTTCTCTCAGTC-3', see also SEQ ID NO: 44) and IFS1:BAA-mature Pps PCR2 (5'-CCATGGT ACCTTAACAGTTAAAATAACAGAAGCACATGTG-3', see also SEQ ID NO: 45).

The reaction mixture contained 12.5 ul of 2× One-step RT-PCR reaction mix, 0.5 μl of each primer (10 μM), 0.5 μl of RT/Platinum Taq mix in a total volume of 15 μl. RT-PCR was performed using the following conditions: 50° C. 30 minutes, 94° C. 2 minutes followed by 35 cycles of 94° C. 30 seconds, 60° C. 1 minute, 72° C. 1 minute, and one cycle of 72° C. 5 minutes. RT-PCR products were visualized on a 1.5% agarose gel.

The results of these analyses demonstrated that the subset of transgenic events tested were expressing detectable levels of Pps-Amp1 mature peptide.

Example 17

T0 SCN Bioassay of Transgenic Events Containing the Mature Pps-AMP1 Peptide

Race 1 *Heterodera glycines* Soybean Cyst Nematodes (SCN) were used to infest transgenic T0 soybean plants in soil. SCN egg inoculum was acquired by harvesting cysts from plants infested 4–6 weeks earlier. Briefly, the soil was rinsed from the roots and passed through nested 20 mesh and 60 mesh screens. The material retained by the 20 mesh screen was discarded but the material retained by the 60 mesh screen was washed thoroughly and the creamy white cysts were recovered (older brown cysts are ignored). Similarly, the plant's root system was scrubbed against the 20 mesh screen nested over the 60 mesh screen. Cysts were harvested from the debris on the 60 mesh screen. Eggs were released from the cysts by means of a dounce homogenizer in the presence of 0.5% Clorox for 2.5 minutes. Following this treatment the eggs were washed with sterile water from the homogenizer onto the surface of a 200 mesh screen. The eggs were then rinsed in water for an additional 5 minutes. Eggs were transferred to a 50 ml conical tube and counted. The eggs were diluted to 5000 eggs/ml. Plants grown in 15 cm conical tubes were inoculated with about 5000 eggs. Plants were maintained in a 26° C. growth chamber with 12:12 light:dark cycle for 1 month prior to harvest and counting of cysts.

Whole plant-bioassays of events containing the nucleotide sequence encoding the mature Pps-AMP1 peptide under control of the UCP1 (see FIG. 3) or IFS1 (see FIG. 4) promoters displayed a range of resistance (as determined by the number of cysts) relative to the negative control (transformed Jack soybean cultivar that did not contain heterologous DNA) and the wild-type Essex cultivar soybean plants. Results from a subset of plants tested are shown in FIGS. 3 and 4. The results of the full set of plants tested appears in Appendix 1 and 2. This range of resistance (based on cyst number) is expected for the population of events generated since differences in Pps-AMP1 mature peptide expression levels may be variable depending on such parameters as, integration site and copy number, among others. While there was a reduction in cyst numbers with both constructs compared to the negative control Jack cultivar or the Essex cultivar, in general, those events containing the Pps-AMP1 mature peptide encoding nucleotide sequence operatively linked to the IFS1 promoter (IFS1:BAA-mature Pps-AMP1) performed better than those events containing the Pps-AMP1 mature peptide encoding nucleotide sequence operatively linked to the UCP1 promoter (UCP1:BAA-mature Pps-AMP1). Several events exhibited excellent resistance with no cysts observed in the root systems.

Example 18

T0 *Sclerotinia sclerotiorum* Detached Leaf Bioassay of Transgenic Events Containing the Pps-AMP1 Mature Peptide Sclerotinia cultures were maintained on ⅛ strength potato dextrose agar (PDA) plates at room temperature in the dark. Cultures were grown by removing 5 mm agar plugs from the maintainence plates and placing the plugs hyphae side down on new PDA plates. Cultures were allowed to grow as indicated above for 3 days. Two individual leaves from 3 plants per event were inoculated with a 5 mm agar plug removed from the growing edge of the culture. Leaves were placed bottom side up on moistened cotton pads in 100×100 mm square Petri plates. Leaves were inoculated by placing the plug, hyphae side down, in the center of leaf. Plates were covered with a lid and incubated in the dark at room temperature. Evaluation of the bioassay was performed 3 days post-inoculation by measuring lesion size (the product of multiplying the diameter of each lesion in 2 directions).

The results of the *Sclerotinia* detached leaf assay with selected UCP1:BAA-mature Pps-AMP1 events (see FIG. 5) and selected IFS1:BAA-mature Pps-AMP1 events (see FIG. 6) also show the expected variability among the events tested. Results from the full set of events is shown in Appendix 3 and 4. Overall some reduction in lesion size relative to the negative control Jack cultivar or the Essex cultivar were observed in the UCP1:BAA-mature Pps-AMP1 events. However, the effect of PpsAMP1 mature peptide on Sclerotina infection was even more significant in the IFS1:BAA-mature Pps-AMP1 events. The IFS1:BAA-mature Pps-AMP1 events exhibited lesion sizes that were either greatly reduced or absent altogether. Inspection of the agar plugs in those events showing reduced or no lesions demonstrated that hyphal growth was evident and in several instances were inhibited at the junction between agar plug and leaf. These results are consistent with the expected relative strength of the two promoters used since the IFS1 promoter is a strong stress-inducible promoter in aerial tissue which is presumably responding to infection by *Sclerotinia* and the UCP1 promoter is a constitutive promoter which does not express as strongly as the IFS1 promoter.

Example 19

Bioassay for Testing the Pesticidal Activity of the Proteins of the Invention Against Southern Corn Rootworm (SCRW) and Western Corn Rootworm (WCRW)

Bio-Serv diet (catalog number F9800B, from: BIOSERV, Entomology Division, One 8th Street, Suite 1, Frenchtown, N.J. 08825) is dispensed in 128-well CD International Bioassay trays (catalog number BIO-BA-128 from CD International, Pitman, N.J. 08071).

Protein samples are applied topically to the diet surface. Enough sample material is supplied to provide for replicate observations per sample. The trays are allowed to dry. Rootworm larvae are dispensed into the wells of the bioassay trays. A lid (catalog number BIO-CV-16, CD International, Pitman, N.J., 08071) is placed on each tray, and the trays are placed in an incubator at 26° C. for 4 to 7 days.

For the evaluation of pesticidal activity against SCRW and WCRW, insects are exposed to a solution comprising either buffer (50 mM carbonate buffer (pH 10)) or a solution of protein sample at selected doses, for example, 50 or 5.0 $\mu g/cm^2$.

The bioassays are then scored by counting "live" versus "dead" larvae. Mortality is calculated as a percentage of dead larvae out of the total number of larvae tested.

Example 20

Bioassay for Testing the Pesticidal Activity of the Proteins of the Invention Against the Colorado Potato Beetle (*Leptinotarsa decemlineata*)

Briefly, bioassay parameters are as follows: Bio-Serv diet (catalog number F9800B, from: BIOSERV, Entomology Division, One 8th Street, Suite 1, Frenchtown, N.J. 08825) is dispensed in a 96 well microtiter plate (catalog number 353918, Becton Dickinson, Franklin Lakes, N.J. 07417–1886) having a surface area of 0.33 $cm^2$. Protein samples of the invention are applied topically to the diet surface. Enough sample material is supplied to provide for 8 observations/sample. After the samples dry, 1 Colorado potato beetle neonate is added to each well providing for a total of 8 larvae/sample. A Mylar® lid (Clear Lam Packaging, Inc., 1950 Pratt Blvd., Elk Grove Village, Ill. 60007-5993) is affixed to each tray. Bioassay trays are placed in an incubator at 25° C. The test is scored for mortality on the 7th day following live infesting.

Example 21

Bioassay for Testing the Pesticidal Activity of the Proteins of the Invention Against Lepidopterans Neonate larvae are reared according to standard protocols, such as those published by Czapla and Lang (1990) *J. Economic Entomology* 83: 2480–2485. Test compounds are either applied topically to the diet or incorporated into the larvae diet (see Czapla and Lang (1990) *Economic Entomology* 83; 2480–2485. The larvae diet is dispensed to bioassay trays. One larva is applied per well of the bioassay tray. Weight and mortality are recorded 7 days following the start of the test.

Example 22

Homopteran Membrane Feeding Bioassay for Screening Proteins of the Invention

This assay can be used for a variety of homopterans. The assay involves trapping the sample protein between two layers of maximally stretched parafilm which act as a sachet on top of a small vessel containing the insect of choice.

The assay is prepared as follows: 1 cm diameter polystyrene tubing is cut into 15 mm lengths. One end of the tube is then capped with a fine mesh screen. Five insects are then added to the chamber after which the first layer of parafilm is stretched over the remaining open end. 25 $\mu l$ of sample (polypeptide in a 5% sucrose solution containing McCormick green food coloring) is then placed on top of the stretched parafilm. A second layer of parafilm is then stretched by hand and placed over the sample. The sample is spread between the two layers of parafilm to make a continuous sachet on which the insects feed. The sachet is then covered tightly with saran wrap to prevent evaporation and produce a slightly pressurized sample. The assay tubes are monitored for insect reproduction and death on a 24 hour basis and compared to the 5% sucrose control.

All publications, patents and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference.

Although the foregoing invention has been described in some detail by way of llustration and example for purposes of clarity of understanding, it will be obvious that certain changes and modifications may be practiced within the scope of the appended claims.

APPENDIX 1

SCN (Race1) whole plant bioassay on transgenic events containing the Pps-AMP1 mature peptide operatively linked to Barley Alpha Amylase signal peptide and driven by the UPCI promoter
TRANSPLANT DATE: JAN. 31, 2002
INOCULATION DATE: FEB. 1, 2002
INOCULATION METHOD: DISPENSE 5000 SCN EGGS 1" BELOW SOIL SURFACE NEAR ROOTS
EVALUATION DATE: MAR. 7, 2002

| EVENT # | CYST # |
|---|---|
| 3177-2-3-1 | 240 |
| 3177-2-3-2 | 60 |
| 3177-2-3-3 | 15 |
| 3177-2-1-1 | 130 |
| 3177-2-1-2 | 82 |
| 3177-2-1-3 | 120 |
| 3177-4-2-1 | 51 |
| 3177-4-2-2 | NO PLANT |
| 3177-4-2-3 | 65 |
| 3177-3-3-1 | 120 |
| 3177-3-3-2 | 8 |
| 3177-3-3-3 | 160 |
| 3177-3-5-1 | 16 |
| 3177-3-5-2 | 85 |
| 3177-3-5-3 | 63 |
| 3177-6-2-1 | 54 |
| 3177-6-2-2 | 43 |
| 3177-6-2-3 | 200 |
| 3177-5-2-1 | 0 |
| 3177-5-2-2 | NO PLANT |
| 3177-5-2-3 | 125 |
| 3177-1-3-1 | 50 |
| 3177-1-3-2 | 66 |
| 3177-1-3-3 | 144 |
| 3177-5-4-1 | 26 |
| 3177-5-4-2 | 22 |
| 3177-5-4-3 | 120 |
| 3177-2-4-1 | 95 |
| 3177-2-4-2 | 55 |
| 3177-2-4-3 | 57 |
| 3177-5-1-1 | 115 |
| 3177-5-1-2 | 14 |
| 3177-5-1-3 | 67 |
| 3177-1-2-1 neg control | 255 |
| 3177-1-2-2 | 170 |
| 3177-1-2-3 | 62 |
| 3178-5-2-1 | 76 |
| 3178-5-2-2 | 44 |
| 3178-5-2-3 | 27 |
| 3178-4-2-1 | 110 |
| 3178-4-2-2 | 19 |
| 3178-4-2-3 | 53 |
| 3178-4-2-4 | 8 |

APPENDIX 1-continued

SCN (Race1) whole plant bioassay on transgenic events containing the Pps-AMP1 mature peptide operatively linked to Barley Alpha Amylase signal peptide and driven by the UPCI promoter
TRANSPLANT DATE: JAN. 31, 2002
INOCULATION DATE: FEB. 1, 2002
INOCULATION METHOD: DISPENSE 5000 SCN EGGS 1" BELOW SOIL SURFACE NEAR ROOTS
EVALUATION DATE: MAR. 7, 2002

| EVENT # | CYST # |
|---|---|
| 3178-1-1-1 | 107 |
| 3178-1-1-2 | 34 |
| 3178-1-1-3 | 81 |
| 3178-5-1-1 | 110 |
| 3178-5-1-2 | 220 |
| 3178-5-1-3 | 21 |
| 3178-6-1-1 | 0 |
| 3178-6-1-2 | 102 |
| 3178-6-1-3 | 0 |
| 3178-4-1-1 | 85 |
| 3178-4-1-2 | 3 |
| 3178-4-1-3 | 25 |
| 3178-1-2-1 | 190 |
| 3178-1-2-2 | 110 |
| 3178-1-2-3 | 37 |
| 3178-4-3-1 | 120 |
| 3178-4-3-2 | 0 |
| 3178-4-3-3 | 59 |
| 3178-5-5-1 | 53 |
| 3178-5-5-2 | 29 |
| 3178-1-3-1 | 34 |
| 3178-1-3-2 | 16 |
| 3178-1-3-3 | 0 |
| ESSEX | 230 |
| ESSEX | 155 |
| ESSEX | 90 |

APPENDIX 2

SCN (Race1) whole plant bioassay on transgenic events containing the Pps-AMP1 mature peptide operatively linked to Barley Alpha Amylase signal peptide and driven by the IFS promoter
INOCULATION DATE: MAR. 8, 2002
EVALUATION DATE: APR. 8, 2002
INOCULATION METHOD: DISPENSE 5000 EGGS 1" BELOW SOIL SURFACE

| EVENT # | CYST # | |
|---|---|---|
| 3193-6-4-1 | 195 | |
| 3193-6-4-2 | 255 | |
| 3193-6-4-3 | | |
| 3192-3-1-1 | 10 | |
| 3192-3-1-2 | 228 | |
| 3192-3-1-3 | | |
| 3192-3-2-1 | 16 | |
| 3192-3-2-2 | 103 | |
| 3192-3-2-3 | 7 | |
| 3192-3-4-1 | 23 | |
| 3192-3-4-2 | 0 | |
| 3192-3-4-3 | 0 | |
| 3192-4-1-1 | 264 | |
| 3192-4-1-2 | 93 | |
| 3192-4-1-3 | 18 | |
| 3192-5-3-1 | | |
| 3192-5-3-2 | 0 | POOR ROOTS |
| 3192-5-3-3 | 0 | POOR ROOTS |
| 3192-6-1-1 | 37 | |
| 3192-6-1-2 | 311 | |
| 3192-6-1-3 | 143 | |
| 3192-6-8-1 | 189 | |
| 3192-6-8-2 | 74 | |
| 3192-6-8-3 | | |
| 3192-6-10-1 | 236 | |
| 3192-6-10-2 | 385 | |

APPENDIX 2-continued

SCN (Race1) whole plant bioassay on transgenic events containing the Pps-AMP1 mature peptide operatively linked to Barley Alpha Amylase signal peptide and driven by the IFS promoter
INOCULATION DATE: MAR. 8, 2002
EVALUATION DATE: APR. 8, 2002
INOCULATION METHOD: DISPENSE 5000 EGGS 1" BELOW SOIL SURFACE

| EVENT # | CYST # | |
|---|---|---|
| 3192-6-10-3 | 275 | |
| 3193-1-1-1 | 128 | |
| 3193-1-1-2 | 79 | |
| 3193-1-1-3 | 170 | |
| 3193-1-4-1 | 49 | |
| 3193-1-4-2 | 0 | NO ROOTS |
| 3193-1-4-3 | 83 | |
| 3193-1-10-1 | 160 | |
| 3193-1-10-2 | 28 | |
| 3193-1-10-3 | 275 | |
| 3193-2-1-1 | 52 | |
| 3193-2-1-2 | 41 | |
| 3193-2-1-3 | 203 | |
| 3193-2-3-1 | 116 | |
| 3193-2-3-2 | 203 | |
| 3193-2-3-3 | 112 | |
| 3193-2-5-1 | 70 | |
| 3193-2-5-2 | 10 | |
| 3193-2-5-3 | 3 | |
| 3193-3-4-1 | 98 | |
| 3193-3-4-2 | 210 | |
| 3193-3-4-3 | 0 | POOR ROOTS |
| 3193-3-5-1 | 3 | POOR ROOTS |
| 3193-3-5-2 | 81 | |
| 3193-3-5-3 | 64 | |
| ESSEX | 110 | |
| ESSEX | 207 | |
| ESSEX | 99 | |

APPENDIX 3

Detached leaf assay on transgenic events containing the Pps-AMP1 mature peptide operatively linked to Barley Alpha Amylase signal peptide and driven by the UPCI promoter
UCP:BAA:PPS-AMP1-SCLEROTINIA DETACHED LEAF BIOASSY
TRANSPLANT DATE: JAN. 31, 2002
INOCULATION DATE: FEB. 5, 2002
EVALUATION DATE: FEB. 8, 2002
LESION SIZE - MEASURED IN MM.

| EVENT # | LESION AREA REP 1 | LESION AREA REP 2 |
|---|---|---|
| 3177-2-3-1 | 15 × 21 = 315 | 19 × 17 = 323 |
| 3177-2-3-2 | 18 × 18 = 324 | 15 × 18 = 270 |
| 3177-2-3-3 | 10 × 10 = 100 | 14 × 25 = 350 |
| 3177-2-1-1 | 16 × 21 = 336 | 21 × 19 = 399 |
| 3177-2-1-2 | 25 × 17 = 425 | 28 × 20 = 560 |
| 3177-2-1-3 | 21 × 17 = 357 | 23 × 27 = 621 |
| 3177-4-2-1 | 18 × 28 = 504 | 24 × 22 = 528 |
| 3177-4-2-2 | NO PLANT | |
| 3177-4-2-3 | 13 × 20 = 260 | 18 × 30 = 540 |
| 3177-3-3-1 | 19 × 22 = 418 | 21 × 21 = 441 |
| 3177-3-3-2 | 20 × 16 = 320 | 19 × 17 = 323 |
| 3177-3-3-3 | 29 × 21 = 609 | 32 × 21 = 672 |
| 3177-3-5-1 | 21 × 18 = 378 | 26 × 19 = 494 |
| 3177-3-5-2 | 11 × 15 = 165 | 18 × 18 = 324 |
| 3177-3-5-3 | 20 × 36 = 720 | 32 × 18 = 576 |
| 3177-6-2-1 | 18 × 29 = 522 | 22 × 30 = 660 |
| 3177-6-2-2 | 10 × 19 = 190 | 11 × 29 = 319 |
| 3177-6-2-3 | 16 × 20 = 320 | 17 × 24 = 408 |
| 3177-5-2-1 | 16 × 18 = 288 | 14 × 12 = 168 |
| 3177-5-2-2 | 21 × 27 = 567 | 22 × 16 = 352 |
| 3177-5-2-3 | 13 × 20 = 260 | 16 × 11 = 176 |
| 3177-1-3-1 | 14 × 12 = 168 | 10 × 9 = 90 |

APPENDIX 3-continued

Detached leaf assay on transgenic events containing the Pps-AMP1 mature peptide operatively linked to Barley Alpha Amylase signal peptide and driven by the UPCI promoter
UCP:BAA:PPS-AMP1-SCLEROTINIA DETACHED LEAF BIOASSY
TRANSPLANT DATE: JAN. 31, 2002
INOCULATION DATE: FEB. 5, 2002
EVALUATION DATE: FEB. 8, 2002
LESION SIZE - MEASURED IN MM.

| EVENT # | LESION AREA REP 1 | LESION AREA REP 2 |
|---|---|---|
| 3177-1-3-2 | 23 × 33 = 759 | 25 × 17 = 425 |
| 3177-1-3-3 | 34 × 20 = 680 | 20 × 14 = 280 |
| 3177-5-4-1 | 17 × 22 = 374 | 18 × 17 = 306 |
| 3177-5-4-2 | 16 × 25 = 400 | 16 × 18 = 288 |
| 3177-5-4-3 | 29 × 213 = 667 | 28 × 20 = 560 |
| 3177-2-4-1 | 17 × 24 = 408 | 15 × 21 = 315 |
| 3177-2-4-2 | 13 × 19 = 247 | 13 × 26 = 338 |
| 3177-2-4-3 | 12 × 17 = 204 | 28 × 9 = 252 |
| 3177-5-1-1 | 22 × 16 = 352 | 18 × 27 = 486 |
| 3177-5-1-2 | 10 × 12 = 120 | 15 × 18 = 270 |
| 3177-5-1-3 | 10 × 14 = 140 | 10 × 12 = 120 |
| 3178-5-2-1 | 15 × 13 = 195 | 21 × 28 = 588 |
| 3178-5-2-2 | 32 × 21 = 672 | 39 × 22 = 858 |
| 3178-5-2-3 | 21 × 28 = 588 | 30 × 20 = 600 |
| 3178-4-2-1 | 14 × 14 = 196 | 18 × 17 = 306 |
| 3178-4-2-2 | 27 × 16 = 432 | 21 × 15 = 315 |
| 3178-4-2-3 | 18 × 33 = 594 | 26 × 20 = 520 |
| 3178-4-2-4 | 20 × 17 = 340 | 21 × 18 = 378 |
| 3178-1-1-1 | 20 × 27 = 540 | 32 × 21 = 672 |
| 3178-1-1-2 | 21 × 20 = 420 | 16 × 19 = 304 |
| 3178-1-1-3 | 23 × 28 = 644 | 27 × 17 = 729 |
| 3178-5-1-1 | 18 × 27 = 486 | 27 × 17 = 459 |
| 3178-5-1-2 | 20 × 28 = 560 | 18 × 17 = 306 |
| 3178-5-1-3 | 15 × 23 = 345 | 17 × 17 = 289 |
| 3178-6-1-1 | 13 × 13 = 169 | 12 × 14 = 168 |
| 3178-6-1-2 | 14 × 15 = 210 | 12 × 19 = 228 |
| 3178-6-1-3 | 20 × 18 = 360 | 20 × 15 = 300 |
| 3178-4-1-1 | 18 × 18 = 324 | 18 × 26 = 468 |
| 3178-4-1-2 | 21 × 22 = 462 | 19 × 14 = 266 |
| 3178-4-1-3 | 10 × 10 = 100 | 22 × 11 = 242 |
| 3178-1-2-1 | 21 × 25 = 525 | 25 × 19 = 475 |
| 3178-1-2-2 | 13 × 13 = 169 | 20 × 12 = 240 |
| 3178-1-2-3 | 18 × 19 = 342 | 20 × 27 = 540 |
| 3178-4-3-1 | 32 × 19 = 608 | 15 × 23 = 345 |
| 3178-4-3-2 | 14 × 14 = 196 | 11 × 14 = 154 |
| 3178-4-3-3 | 19 × 20 = 380 | 27 × 18 = 486 |
| 3178-5-5-1 | 38 × 26 = 988 | 31 × 21 = 651 |
| 3178-5-5-2 | 21 × 18 = 378 | 17 × 21 = 357 |
| 3178-1-3-1 | 16 × 21 = 336 | 20 × 19 = 380 |
| 3178-1-3-2 | 23 × 26 = 598 | 14 × 25 = 350 |
| 3178-1-3-3 | 32 × 19 = 608 | 33 × 21 = 714 |
| ESSEX | 37 × 24 = 888 | 34 × 21 = 714 |
| | 20 × 31 = 620 | 23 × 21 = 483 |
| NEG CONTROLS | | |
| 3177-1-2-1 | 19 × 26 = 494 | 17 × 21 = 357 |
| 3177-1-2-2 | 25 × 22 = 550 | 22 × 21 = 462 |
| 3177-1-2-3 | 20 × 18 = 360 | 31 × 20 = 620 |

APPENDIX 4

Detached leaf assay on transgenic events containing the Pps-AMP1 mature peptide operatively linked to Barley Alpha Amylase signal peptide and driven by the IFS promoter
IFS:BAA:PPS-AMP1-SCLEROTINIA DETACHED LEAF BIOASSY
INOCULATION DATE: MAR. 26, 2002
EVALUATION DATE: MAR. 29, 2002
LESION SIZE - MEASURED IN MM.

| EVENT # | LESION AREA REP 1 | LESION AREA REP 2 |
|---|---|---|
| 3192-2-1-4 | 0 | 0 |
| 3192-2-1-5 | 0 | 50 |
| 3192-2-1-6 | 0 | 0 |
| 3192-3-1-5 | 4 | 6 |
| 3192-3-1-6 | 110 | 54 |
| 3192-3-2-4 | 0 | RIB |
| 3192-3-2-5 | 0 | 0 |
| 3192-3-2-6 | SPOTS | SPOTS |
| 3192-3-4-4 | 0 | SPOTS |
| 3192-3-4-5 | 4 | 120 |
| 3192-4-1-4 | 0 | 0 |
| 3192-4-1-5 | 0 | 450 |
| 3192-4-1-6 | VEIN | 225 |
| 3192-5-3-4 | 0 | 0 |
| 3192-5-3-5 | 0 | 49 |
| 3192-6-1-5 | 0 | 0 |
| 3192-6-1-6 | 0 W/ SPOTS | 126 |
| 3192-6-8-4 | 0 | 0 |
| 3192-6-8-5 | 8 | 6 |
| 3192-6-8-6 | SPOTS | SPOTS |
| 3192-6-10-4 | 4 | 100 |
| 3192-6-10-5 | 25 | 70 |
| 3192-6-10-6 | 0 | 0 |
| ESSEX | 224 | 195 |
| ESSEX | 100 | 156 |
| ESSEX | 270 | 110 |
| 3193-1-1-4 | 20 | 0 W/ SPOTS |
| 3193-1-1-5 | 0 | 0 |
| 3193-1-1-6 | 70 | 80 |
| 3193-1-4-4 | 132 | 90 |
| 3193-1-4-5 | 168 | 168 |
| 3193-1-4-6 | 0 | 192 |
| 3193-1-10-4 | 15 | 99 |
| 3193-1-10-5 | SPOTS | 0 |

APPENDIX 4-continued

Detached leaf assay on transgenic events containing the Pps-AMP1 mature peptide operatively linked to Barley Alpha Amylase signal peptide and driven by the IFS promoter
IFS:BAA:PPS-AMP1-SCLEROTINIA DETACHED LEAF BIOASSY
INOCULATION DATE: MAR. 26, 2002
EVALUATION DATE: MAR. 29, 2002
LESION SIZE - MEASURED IN MM.

| EVENT # | LESION AREA REP 1 | LESION AREA REP 2 |
|---|---|---|
| 3193-1-10-6 | 0 | 0 |
| 3193-2-1-4 | 4 | 60 |
| 3193-2-1-5 | 0 | 0 |
| 3193-2-1-6 | 0 | 0 |
| 3193-2-3-4 | 15 | 99 |
| 3193-2-3-5 | 0 | 0 |
| 3193-2-3-6 | 0 | 0 |
| 3193-2-5-4 | 260 | 208 |
| 3193-2-5-6 | 0 | 0 |
| 3193-3-4-4 | 162 | 156 |
| 3193-3-4-5 | 0 | 0 |
| 3193-3-4-6 | 0 | 20 |
| 3193-3-5-4 | 150 | 56 |
| 3193-3-5-5 | 25 | 25 |
| 3193-3-5-6 | 0 | 0 W/ SPOTS |
| 3193-5-1-4 | 0 | 0 |
| 3193-5-1-5 | 91 | 117 |
| 3193-6-4-5 | RIB | 20 |
| 3193-6-4-6 | 0 | 0 |
| NEG CONTROLS | | |
| 3193-4-5-4 | 0 | 0 |
| 3193-4-5-5 | 0 | 0 |
| 3193-4-5-6 | 600 | 450 |

That which is claimed:

1. An isolated nucleic acid molecule comprising a nucleotide sequence selected from the group consisting of:

(a) a nucleotide sequence having at least 80% sequence identity to SEQ ID NO: 7, SEQ ID NO: 29, or SEQ ID NO: 34 wherein said nucleotide sequence encodes a polypeptide having defensin activity against at least one pathogen; and (b) a nucleotide sequence that comprises the complement of (a).

2. The nucleic acid molecule according to claim 1, wherein the nucleotide sequence is optimized for expression in a plant.

3. A DNA construct comprising the nucleic acid molecule of claim 1, wherein said nucleotide sequence is operably linked to a promoter that drives expresion in a host cell.

4. The nucleic acid molecule of claim 1, wherein said nucleotide sequence has at least 95% sequence identity to SEQ ID NO: 7, SEQ ID NO: 29, or SEQ ID NO: 34 and encodes a polypeptide having defensin activity against at least one pathogen.

5. A host cell having stably incorporated into its genome at least one DNA construct of claim 3.

6. The host cell of claim 5, wherein said host cell is a plant cell.

7. A plant having stably incorporated into its genome the DNA construct of claim 3.

8. The plant according to claim 7, wherein said plant is a monocot.

9. The plant according to claim 7, wherein said plant is a dicot.

10. Transformed seed of the plant of claim 7.

11. A method for impacting resistance of a plant to at least one pathogen comprising introducing into a plant at least one DNA construct comprising a nucleotide sequence operably linked to a promoter that drives expression in a plant cell, wherein said nucleotide sequence is selected from the group consisting of:

(a) a nucleotide sequence having at least 80% sequence identity to SEQ ID NO: 7, SEQ ID NO: 29, or SEQ ID NO: 34, wherein said nucleotide sequence encodes a polypeptide having defensin activity against at least one pathogen; and (b) a nucleotide sequence that comprises the complement of (a).

12. The method of claim 11, wherein said plant produces a polypeptide having defensin activity against at least one pathogen.

13. The method of claim 12, wherein said pathogen is a fungus.

14. The method of claim 13, wherein said fungus is *Sclerotinia sclerotiorum.*

15. The method of claim 11, wherein said plant produces a polypeptide having pesticidal activity against at least one insect pest.

16. The method of claim 11, wherein said plant produces a polypeptide having pesticidal activity against at least one nematode.

17. The method of claim 16, wherein said nematode is a Soybean Cyst Nematode.

18. A method for enhancing resistance of a plant or cell thereof to the fungal pathogen *Sclerotinia sclerotiorum* comprising introducing into a plant or cell thereof at least one DNA construct comprising a nucleotide sequence operably linked to a promoter that drives expression in a plant cell, wherein said nucleotide sequence has at least 80% sequence identity to SEQ ID NO: 7, SEQ ID NO: 29, or SEQ ID NO: 34 and encodes a polypeptide having defensin activity against *Sclerotinia sclerotiorum.*

19. The method of claim 18, wherein said nucleotide sequence has at least 90% sequence identity to SEQ ID NO: 7, SEQ ID NO: 29, or SEQ ID NO: 34.

20. The method of claim 18, wherein said nucleotide sequence has at least 95% sequence identity to SEQ ID NO: 7, SEQ ID NO: 29, or SEQ ID NO: 34.

21. A method for enhancing resistance of a plant or cell thereof to at least one nematode comprising introducing into a plant or cell thereof at least one DNA construct comprising a nucleotide sequence operably linked to a promoter that drives expression in a plant cell, wherein said nucleotide sequence has at least 80% sequence identity to SEQ ID NO:

7, SEQ ID NO: 29, or SEQ ID NO: 34 and encodes a polypeptide having defensin activity against said nematode.

22. The method of claim 21, wherein said nematode is the Soybean Cyst Nematode.

23. The method of claim 21, wherein said nucleotide sequence has at least 90% sequence identity to SEQ ID NO: 7, SEQ ID NO: 29, or SEQ ID NO: 34.

24. The method of claim 21, wherein said nucleotide sequence has at least 95% sequence identity to SEQ ID NO: 7, SEQ ID NO: 29, or SEQ ID NO: 34.

25. The nucleic acid molecule according to claim 1 comprising the nucleotide sequence as set forth in SEQ ID NO7.

26. The nucleic acid molecule according to claim 1 comprising the nucleotide sequence as set forth in SEQ ID NO:29.

27. The nucleic acid molecule according to claim 1 comprising the nucleotide sequence as set forth in SEQ ID NO:34.

28. The nucleic acid molecule according to claim 1. comprising a nucleolide sequence that encodes a polypeptide having the amino acid sequence set forth in SEQ ID NO:30.

29. The nucleic acid molocule according to claim 1 comprising a nucleotide sequence that encodes a polypeptide having the amino acid sequence set forth in SEQ ID NO:35.

30. The method according to claim 11, wherein the nucleotide sequence comprises SEQ ID NO:7.

31. The method according to claim 11, wherein the nucleotide sequence comprises SEQ ID NO:29.

32. The method according to claim 11, wherein the nucleotide sequence comprises SEQ ID NO:34.

33. The method according to claim 11, wherein the nucleotide sequence encodes a polypeptide having the amino acid sequence set forth in SEQ ID NO:30.

34. The method according to claim 11, wherein the nucleotide sequence encodes a polypeptide having the amino acid sequence set forth in SEQ ID NO:35.

35. The nucleic acid molecule according to claim 1, wherein the nucleotide sequence encodes a polypeptide having the amino acid sequence set forth in SEQ ID NO: 8.

36. The method according to claim 11, wherein the nucleotide sequence encodes a polypeptide having the amino acid sequence set forth in SEQ ID NO:8.

37. An isolated nucleic acid molecule comprising a nucleotide sequence selected from the group consisting of:

(a) a nucleotide sequence having at least 85% sequence identity to SEQ ID NO: 7, SEQ ID NO: 29, or SEQ ID NO: 34 wherein said nucleotide sequence encodes a polypeptide having defensin activity against at least one pathogen; and (b) a nucleotide sequence that comprises the complement of (a).

38. An isolated nucleic acid molecule comprising a nucleotide sequence selected from the group consisting of:

(a) a nucleotide sequence having at least 90% sequence identity to SEQ ID NO: 7, SEQ ID NO: 29, or SEQ ID NO: 34 wherein said nucleotide sequence encodes a polypeptide having defensin activity against at least one pathogen; and (b) a nucleotide sequence that comprises the complement of (a).

39. A method for impacting resistance of a plant to at least one pathogen comprising introducing into a plant at least one DNA construct comprising a nucleotide sequence operably linked to a promoter that drives expression in a plant cell, wherein said nucleotide sequence is selected from the group consisting of:

(a) a nucleotide sequence having at least 85% sequence identity to SEQ ID NO: 7, SEQ ID NO: 29, or SEQ ID NO: 34, wherein said nucleotide sequence encodes a polypeptide having defensin activity against at least one pathogen; and (b) a nucleotide sequence that comprises the complement of (a).

40. A method for impacting resistance of a plant to at least one pathogen comprising introducing into a plant at least one DNA construct comprising a nucleotide sequence operably linked to a promoter that drives expression in a plant cell, wherein said nucleotide sequence is selected from the group consisting of:

(a) a nucleotide sequence having at least 90% sequence identity to SEQ ID NO: 7, SEQ ID NO: 29, or SEQ ID NO: 34, wherein said nucleotide sequence encodes a polypeptide having defensin activity against at least one pathogen; and (b) a nucleotide sequence that comprises the complement of (a).

41. The method of claim 11, wherein said nucleotide sequence has at least 95% sequence identity to SEQ ID NO: 7, SEQ ID NO: 29, or SEQ ID NO: 34.

* * * * *